(12) United States Patent
Reader

(10) Patent No.: US 9,133,180 B2
(45) Date of Patent: Sep. 15, 2015

(54) AURORA AND FLT3 KINASES MODULATORS

(71) Applicant: SAREUM LIMITED, Cambridge (GB)

(72) Inventor: John Charles Reader, Cambridge (GB)

(73) Assignee: SAREUM LIMITED (GB)

( * ) Notice: Subject to any disclaimer, the term of this patent is extended or adjusted under 35 U.S.C. 154(b) by 0 days.

(21) Appl. No.: 14/376,729

(22) PCT Filed: Feb. 4, 2013

(86) PCT No.: PCT/EP2013/052182
§ 371 (c)(1),
(2) Date: Aug. 5, 2014

(87) PCT Pub. No.: WO2013/117522
PCT Pub. Date: Aug. 15, 2013

(65) Prior Publication Data
US 2015/0018367 A1 Jan. 15, 2015

(30) Foreign Application Priority Data
Feb. 6, 2012 (GB) .................................. 1202027.7

(51) Int. Cl.
A61K 31/496 (2006.01)
C07D 413/14 (2006.01)
A61K 45/06 (2006.01)

(52) U.S. Cl.
CPC ............ C07D 413/14 (2013.01); A61K 31/496 (2013.01); A61K 45/06 (2013.01)

(58) Field of Classification Search
CPC ..... C07D 413/14; A61K 31/496; A61K 45/06
See application file for complete search history.

(56) References Cited

U.S. PATENT DOCUMENTS

| 7,125,891 | B2 | 10/2006 | Breslin et al. |
| 8,378,095 | B2 | 2/2013 | Reader et al. |
| 8,921,544 | B2 | 12/2014 | Reader et al. |
| 2013/0102592 | A1 | 4/2013 | Reader et al. |
| 2013/0231340 | A1 | 9/2013 | Reader |

FOREIGN PATENT DOCUMENTS

| CN | 1950347 | A | 4/2007 |
| DE | 2301030 | | 2/1974 |
| DE | 19653355 | A1 | 6/1998 |
| DK | 200600313 | L | 3/2006 |
| EP | 2634185 | A1 | 9/2013 |
| GB | 1374345 | | 11/1974 |
| JP | 6310767 | A | 11/1994 |
| WO | 0158890 | A1 | 8/2001 |
| WO | 0200649 | A1 | 1/2002 |
| WO | 2004005283 | A1 | 1/2004 |
| WO | 2005040139 | A2 | 5/2005 |
| WO | 2006095159 | A1 | 9/2006 |
| WO | 2007043400 | A1 | 4/2007 |
| WO | 2007131953 | A1 | 11/2007 |
| WO | 2008024980 | A2 | 2/2008 |
| WO | 2008139161 | A1 | 11/2008 |
| WO | WO 2008139161 | A1 * | 11/2008 |
| WO | 2010011375 | A2 | 1/2010 |
| WO | 2010055304 | A2 | 5/2010 |
| WO | 2012021611 | A1 | 2/2012 |

OTHER PUBLICATIONS deVries et al., 92 Haematologica, 1557-1560 (2007).*
D. Gilliland et al., 100 Blood 1532-1542 (2002).*
P. Brown et al., 105 Blood, 812-820 (2005).*
H.K. Lee et al., 123 Blood, 2209-2219 (2014).*
International Search Report for PCT/EP2012/052182 dated Mar. 4, 2013.
Lykkeberg et al., Preparation of Some 2,4-Disubstituted Imidazole-5-carboxamides by Thermolysis of β-Substituted α-(1-Tetrazolyl) acrylamides, Acta Chem. Scand. B29, No. 7, p. 793-5 (1975).
Spiekermann et al., The Protein Tyrosine Kinase Inhibitor SU5614 Inhibits FLT3 and Induces Growth Arrest and Apoptosis in AML-derived Cell Lines Expressing a Constitutively Activated FLT3, Neoplasia, vol. 101, No. 4, p. 1494-1504 (Feb. 15, 2003).
Ponomarev et al., Zhurnal Fizicheskoi Khimii, 64(10), 2723-9, Chem Abs. 114:100938 (1990).
Ozaki et al., Syntheses of 5-Substituted Oxazole-4-Carboxylic Acid Derivatives with Inhibitory Activity on Blood Platelet Aggregation, Chem. Pharm. Bull, No. 12, p. 4417-24 (Apr. 15, 1983).

(Continued)

Primary Examiner — Alexander R Pagano
(74) Attorney, Agent, or Firm — Hestin Rothenberg Farley & Mesiti, P.C.

(57) ABSTRACT

The invention provides a compound having the formula (1):

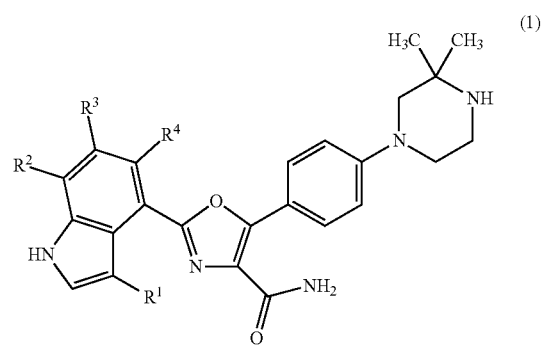

and salts thereof; wherein:
$R^1$ is hydrogen or $C_{1-2}$ alkyl; and
$R^2$, $R^3$ and $R^4$ are the same or different and each is selected from hydrogen, $C_{1-2}$ alkyl, fluorine, chlorine, $C_{1-2}$ alkoxy and trifluoromethyl, provided that no more than two of $R^2$, $R^3$ and $R^4$ are other than hydrogen.

Also provided are pharmaceutical compositions containing the compounds and their use in medicine, and in particular in the treatment of cancer.

15 Claims, 3 Drawing Sheets

(56) References Cited

OTHER PUBLICATIONS

Harrington et al., VX-680, A Potent and Selective Small-Molecule Inhibitor of the Aurora Kinases, Suppresses Tumor Growth in vivo, Nature Medicine, vol. 10, No. 3, p. 262-7 (Mar. 2004).

Franchetti et al., Synthesis and Antitumor Activity of 2-β-D-Ribofuranosyloxazole-4-Carboxamide (Oxazofurin), J. Med. Chem., p. 2849-2852 (1990).

Morwick et al., Evolution of the Thienopyridine Class of Inhibitors of Iκb Kinase-β: Part I: Hit-to-Lead Strategies, J. Med. Chem., 2898-2908 (2006).

Jansen et al., Some 4-Substituted Oxazoles, J. Chem. Soc., p. 405-411 (1961).

* cited by examiner

AURORA AND FLT3 KINASES MODULATORS

CROSS REFERENCE TO RELATED APPLICATIONS

This application is a national phase filing under 35 U.S.C. §371 of PCT International Application PCT/EP2013/052182, filed Feb. 4, 2013, and published in English as WO 2013/117522 A1 on Aug. 15, 2013. PCT/EP2013/052182 claimed priority to British application No. 1202027.7, filed on Feb. 6, 2012. The entire contents of each of the prior applications are hereby incorporated herein by reference.

This invention relates to compounds that inhibit or modulate the activity of kinases, and in particular Aurora kinases and FLT3 kinases, to the use of the compounds in the treatment or prophylaxis of disease states or conditions mediated by kinases. Also provided are pharmaceutical compositions containing the compounds, processes for their preparation and novel chemical intermediates.

BACKGROUND OF THE INVENTION

Protein kinases constitute a large family of structurally related enzymes that are responsible for the control of a wide variety of signal transduction processes within the cell (Hardie and Hanks (1995) *The Protein Kinase Facts Book. I and II*, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks and Hunter, *FASEB J.*, (1995) 9. 576-596; Knighton, et al., *Science*, (1991) 253, 407-414; Hiles, et al., *Cell*, (1992) 70, 419-429; Kunz, et al., *Cell*, (1993) 73, 585-596; Garcia-Bustos, et al., *EMBO J.*, (1994) 13, 2352-2361).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, disease and conditions of the immune system, disease and conditions of the central nervous system, and angiogenesis.

Aurora Kinases

Three members of the Aurora kinase family have been found in mammals so far (Nigg, *Nat. Rev. Mol. Cell Biol.* (2001) 2, 21-32). Aurora A kinase (also referred to in the literature as Aurora 2) is a serine/threonine kinase that is involved in the G2 and M phases of the cell cycle, and is an important regulator of mitosis. Aurora kinase A is believed to play a part in mitotic checkpoint control, chromosome dynamics and cytokinesis (Adams et al., *Trends Cell Biol.*, (2001) 11, 49-54). The kinases are located at the centrosomes of interphase cells, at the poles of the bipolar spindle and in the mid-body of the mitotic apparatus.

The other two currently known Aurora kinases are Aurora B (also referred to in the literature as Aurora 1) and Aurora C (also referred to in the literature as Aurora 3). The Aurora kinases have highly homologous catalytic domains but differ considerably in their N-terminal portions (Katayama et al, *Cancer Metastasis Rev.* (2003) 22(4), 451-64).

The substrates of the Aurora kinases A and B have been identified as including a kinesin-like motor protein, spindle apparatus proteins, histone H3 protein, kinetochore protein and the tumour suppressor protein p53.

Aurora A kinases are believed to be involved in spindle formation and become localised on the centrosome during the early G2 phase where they phosphorylate spindle-associated proteins (Prigent et al., *Cell* (2003) 114, 531-535). Hirota et al, (*Cell*, (2003) 114, 585-598) found that cells depleted of Aurora A protein kinase were unable to enter mitosis. Furthermore, it has been found (Adams, 2001) that mutation or disruption of the Aurora A gene in various species leads to mitotic abnormalities, including centrosome separation and maturation defects, spindle aberrations and chromosome segregation defects.

Aurora kinase A is generally expressed at a low level in the majority of normal tissues, the exceptions being tissues with a high proportion of dividing cells such as the thymus and testis. However, elevated levels of Aurora kinases have been found in many human cancers (Giet et al., *J. Cell. Sci.* (1999) 112, 3591 and Katayama (2003)). Furthermore, Aurora A kinase maps to the chromosome 20q13 region that has frequently been found to be amplified in many human cancers.

Thus, for example, significant Aurora A over-expression has been detected in human breast, ovarian and pancreatic cancers (see Zhou et al., *Nat. Genet.* (1998) 20, 189-193; Tanaka et al., *Cancer Res.* (1999) 59, 2041-2044 and Han et al., *Cancer Res.* (2002) 62, 2890-2896).

Moreover, Isola (*American Journal of Pathology* (1995) 147, 905-911) has reported that amplification of the Aurora A locus (20q13) correlates with poor prognosis for patients with node-negative breast cancer.

Amplification and/or over-expression of Aurora-A is observed in human bladder cancers and amplification of Aurora-A is associated with aneuploidy and aggressive clinical behaviour (see Sen et al., *J. Natl. Cancer Inst.* (2002) 94, 1320-1329).

Elevated expression of Aurora-A has been detected in over 50% of colorectal cancers (see Bischoff et al., *EMBO J.* (1998) 17, 3052-3065 and Takahashi et al., *Jpn. J. Cancer Res.* (2000) 91, 1007-1014), ovarian cancers (see Gritsko et al., *Clin. Cancer Res.* (2003) 9, 1420-1426) and gastric tumours (see Sakakura et al., *British Journal of Cancer* (2001) 84, 824-831).

Tanaka et al., (*Cancer Research* (1999) 59, 2041-2044) found evidence of over-expression of Aurora A in 94% of invasive duct adenocarcinomas of the breast.

High levels of Aurora A kinase have also been found in renal, cervical, neuroblastoma, melanoma, lymphoma, pancreatic and prostate tumour cell lines (Bischoff et al., (1998), *EMBO J.* (1998) 17, 3052-3065; Kimura et al., *J. Biol. Chem.* (1999) 274, 7334-7340; Zhou et al., *Nature Genetics*, 20: 189-193 (1998); Li et al., *Clin Cancer Res.* 9 (3): 991-7 (2003).

Royce et al (*Cancer.* (2004) 100(1), 12-19) report that the expression of the Aurora 2 gene (known as STK15 or BTAK) has been noted in approximately one-fourth of primary breast tumours.

Reichardt et al (*Oncol Rep.* (2003) 10(5), 1275-9) have reported that quantitative DNA analysis by PCR to search for Aurora amplification in gliomas revealed that 5 out of 16 tumours (31%) of different WHO grade (1× grade II, 1× grade III, 3× grade IV) showed DNA amplification of the Aurora 2 gene. It was hypothesized that amplification of the Aurora 2 gene may be a non-random genetic alteration in human gliomas playing a role in the genetic pathways of tumourigenesis.

Results by Hamada et al (*Br. J. Haematol.* (2003) 121(3), 439-47) also suggest that Aurora 2 is an effective candidate to indicate not only disease activity but also tumourigenesis of non-Hodgkin's lymphoma. Retardation of tumour cell growth resulting from the restriction of this gene's functions could be a therapeutic approach for non-Hodgkin's lymphoma.

In a study by Gritsko et al (*Clin Cancer Res.* (2003) 9(4), 1420-6), the kinase activity and protein levels of Aurora A were examined in 92 patients with primary ovarian tumours. In vitro kinase analyses revealed elevated Aurora A kinase activity in 44 cases (48%). Increased Aurora A protein levels were detected in 52 (57%) specimens. High protein levels of Aurora A correlated well with elevated kinase activity.

Results obtained by Li et al (*Clin. Cancer Res.* 2003 March; 9(3):991-7) showed that the Aurora A gene is overexpressed in pancreatic tumours and carcinoma cell lines and suggest that overexpression of Aurora A may play a role in pancreatic carcinogenesis.

Similarly, it has been shown that Aurora A gene amplification and associated increased expression of the mitotic kinase it encodes are associated with aneuploidy and aggressive clinical behaviour in human bladder cancer. (*J. Natl. Cancer Inst.* (2002) 94(17), 1320-9).

Investigation by several groups (Dutertre and Prigent, *Mol. Interv.* (2003) 3(3), 127-30 and Anand et al., *Cancer Cell.* (2003) 3(1), 51-62) suggests that overexpression of Aurora kinase activity is associated with resistance to some current cancer therapies. For example overexpression of Aurora A in mouse embryo fibroblasts can reduce the sensitivity of these cells to the cytotoxic effects of taxane derivatives. Therefore Aurora kinase inhibitors may find particular use in patients who have developed resistance to existing therapies.

On the basis of work carried out to date, it is envisaged that inhibition of Aurora A kinase will prove an effective means of arresting tumour development.

It has also been shown that there is an increase in expression of Aurora B in tumour cells compared to normal cells (Adams et al., *Chromasoma.* (2001) 110, 65-74). One report suggests that overexpression of Aurora B induces aneuploidy through increased phosphorylation of histone H3 at serine 10, and that cells overexpressing Aurora B form more aggressive tumours and have a higher tendency to form metastatic tumours (Ota et al., *Cancer Res.* (2002) 62, 5168-5177).

Aurora B is required for both spindle checkpoint function and metaphase chromosome alignment in human cells (Adams et al. *J. Cell Biol.* (2001) 153, 865-880; Kallio et al., *Curr. Biol.* (2002) 12, 900-905 and Murata-Hori and Wang *Curr. Biol.* (2002) 12, 894-899). It has been demonstrated that suppression of Aurora B kinase activity compromises chromosome alignment, spindle checkpoint function and cytokinesis (Ditchfield et al., *J. Cell Biol.* (2003) 161, 267-280 and Hauf et al., *J. Cell Biol.* (2003), 161, 281-294). Consequently, after a brief delay cells exit mitosis without dividing and with a 4N DNA content, whereupon they rapidly lose their proliferative potential.

Harrington et al (*Nat Med.* (2004) 10(3), 262-7) have demonstrated that an inhibitor of the Aurora kinases suppresses tumour growth and induces tumour regression in vivo. In the study, the Aurora kinase inhibitor blocked cancer cell proliferation, and also triggered cell death in a range of cancer cell lines including leukaemic, colorectal and breast cell lines. In addition, it has shown potential for the treatment of leukemia by inducing apoptosis in leukemia cells. VX-680 potently killed treatment-refractory primary Acute Myelogenous Leukemia (AML) cells from patients (Andrews, *Oncogene* (2005) 24, 5005-5015).

Manfredi et al (*PNAS* (2007) 104, 4106-4111) have demonstrated that a small-molecule inhibitor of Aurora A suppresses tumour growth in vivo. In the study, dose-dependent tumour growth inhibition was demonstrated in HCT-116 tumour bearing mice and PC-3 tumour bearing mice versus vehicle treated mice. Tumour growth inhibition of up to 84% against HCT-116 and 93% against PC-3 cell xenografts was observed.

Mortlock et al (*Clin Cancer Res.* (2007) 13(12), 3682-3688) have demonstrated that a small molecule inhibitor of Aurora B suppresses tumour growth in vivo. Immunodeficient mice bearing established SW620, HCT-116, Colo205, A549, Calu-6 or HL-60 tumour xenografts were dosed over 48 h via sub-cutaneous mini-pump infusion with the small molecule inhibitor AZD1152. The inhibition of tumour growth in all cases ranged from 55% to 100% with complete tumour regression observed in 8 of 11 animals bearing the HL-60 xenograft.

On the basis of evidence obtained to date, it is considered likely that Aurora kinase inhibitors should be particularly useful in arresting tumour development and treating cancers such as breast, bladder, colorectal, pancreatic and ovarian cancers, non-Hodgkin's lymphoma, gliomas, nonendometrioid endometrial carcinomas, Acute Myelogenous Leukemia (AML), Chronic Myelogenous Leukaemia (CML), B-cell lymphoma (Mantle cell), and Acute Lymphoblastic Leukemia (ALL).

FLT3

FMS-like tyrosine kinase 3 (FLT3) is a receptor tyrosine kinase involved in the proliferation, differentiation and apoptosis of hematopoietic and non-hematopoietic cells (Scheijen and Griffin, *Oncogene* (2002) 21, 3314-3333 and Reilly, *British Journal of Haematology* (2002) 116, 744-757). As a result of the natural ligand (FL) binding, the FLT3 receptor dimerises resulting in activation of its tyrosine kinase domain, receptor autophosphorylation and recruitment of downstream signalling molecules such as the p85 subunit of PI3K (phosphatidylinositol 3 kinase), PLC-gamma (Phospholipase-C gamma), STAT5a (signal transducer and activator of transcription 5a), and SRC family tyrosine kinases (Gilliland and Griffin, *Blood* (2002) 100(5), 1532-42; Drexler, *Leukemia* (1996) 10(4), 588-99 and Ravandi et al., *Clin Cancer Res.* (2003) 9(2), 535-50).

Activation of these downstream signalling molecules by phosphorylation leads to the proliferative and pro-survival effects of FLT3 (Gilliland and Griffin (2002) and Levis and Small, *Leukemia* (2003) 17(9), 1738-52).

Somatic mutations of FLT3 involving internal tandem duplications in the juxtamembrane region of the receptor, or through point mutation of D835 in the activation loop have been demonstrated in approximately 30% of patients with acute myeloid leukaemia (AML), a cancer of the white blood cells caused through overproduction of immature myeloid white blood cells (Nakao et al., *Leukemia* (1996) 10(12), 1911-8; Thiede et al., *Blood* (2002) 99(12), 4326-35; Yamamoto et al., *Blood* (2001) 97(8), 2434-9; Abu-Duhier et al., *Br. J. Haematol.* (2000) 111(1), 190-5 and Abu-Duhier et al., *Br. J. Haematol.* (2001) 113(4), 983-8).

Other ligand independent activating mutations of FLT3 have recently been described, contributing to the leukaemic transformation in AML. Presence of such mutations at diagnosis has been linked to inferior prognosis in some patients (Jiang et al., *Blood* (2004) 104(6), 1855-8 and Kindler et al., *Blood* (2005) 105(1), 335-40).

Our earlier International patent application WO2008/139161 discloses a class of substituted oxazole carboxamides as inhibitors of various kinases and in particular Aurora kinase, FLT3 kinase and FLT4 kinase.

Example M-12 on page 132 of WO2008/139161 describes the preparation of the compound 2-(1H-Indol-4-yl)-5-(4-piperazin-1-yl-phenyl)-oxazole-4-carboxylic acid amide which has the structural formula set out below.

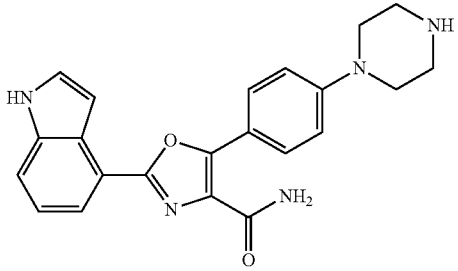

SUMMARY OF THE INVENTION

It has now been found that analogues of the compound shown above, but wherein the $CH_2$ moiety at the 3-position of the piperazine ring is replaced by a $C(CH_3)_2$ moiety, have substantially enhanced potency against one or more kinases selected from Aurora A and Aurora B kinases and FLT3 kinase and have reduced efflux liability compared to the compound of Example M-12 of WO. It has also been found that the potency of the compounds against Aurora kinases is further substantially enhanced by the presence of substituents on the indole group.

Accordingly, in a first embodiment (Embodiment 1.1), the invention provides a compound having the formula (1):

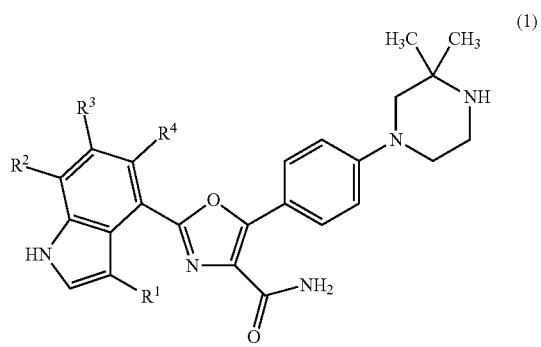

and salts thereof; wherein:

$R^1$ is hydrogen or $C_{1-2}$ alkyl; and
$R^2$, $R^3$ and $R^4$ are the same or different and each is selected from hydrogen, $C_{1-2}$ alkyl, fluorine, chlorine, $C_{1-2}$ alkoxy and trifluoromethyl, provided that no more than two of $R^2$, $R^3$ and $R^4$ are other than hydrogen.

Particular and preferred compounds of the invention are as defined in Embodiments 1.2 to 1.33 below.

1.2 A compound according to Embodiment 1.1 wherein $R^1$ is selected from hydrogen and methyl.

1.3 A compound according to Embodiment 1.2 wherein $R^1$ is hydrogen.

1.4 A compound according to Embodiment 1.2 wherein $R^1$ is methyl.

1.5 A compound according to any one of Embodiments 1.1 to 1.4 wherein $R^2$ is selected from hydrogen, fluorine, chlorine, methyl, ethyl, trifluoromethyl and methoxy.

1.6 A compound according to any one of Embodiments 1.1 to 1.4 wherein $R^2$ is selected from hydrogen, fluorine, chlorine, methyl, ethyl and methoxy.

1.6A A compound according Embodiment 1.6 wherein $R^2$ is selected from hydrogen, fluorine, chlorine, methyl and methoxy 1.7 A compound according to Embodiment 1.5 wherein $R^2$ is hydrogen.

1.8 A compound according to Embodiment 1.5 wherein $R^2$ is fluorine.

1.9 A compound according to Embodiment 1.5 wherein $R^2$ is chlorine.

1.10 A compound according to Embodiment 1.5 wherein $R^2$ is methyl.

1.11 A compound according to Embodiment 1.5 wherein $R^2$ is ethyl.

1.12 A compound according to Embodiment 1.5 wherein $R^2$ is methoxy.

1.13 A compound according to Embodiment 1.5 wherein $R^2$ is trifluoromethyl.

1.14 A compound according to any one of Embodiments 1.1 to 1.13 wherein $R^3$ is selected from hydrogen and fluorine.

1.15 A compound according to Embodiment 1.14 wherein $R^3$ is hydrogen.

1.16 A compound according to any one of Embodiments 1.1 to 1.15 wherein $R^4$ is selected from hydrogen, fluorine, methyl and ethyl.

1.17 A compound according to Embodiment 1.16 wherein $R^4$ is hydrogen.

1.18 A compound according to Embodiment 1.16 wherein $R^4$ is selected from fluorine, methyl and ethyl, and one of $R^2$ and $R^3$ is hydrogen.

1.19 A compound according to Embodiment 1.18 wherein $R^3$ is hydrogen.

1.20 A compound according to Embodiment 1.18 or Embodiment 1.19 wherein $R^4$ is fluorine.

1.21 A compound according to Embodiment 1.18 or Embodiment 1.19 wherein $R^4$ is methyl.

1.22 A compound according to Embodiment 1.18 or Embodiment 1.19 wherein $R^4$ is ethyl.

1.22A A compound according to Embodiment 1.1 wherein $R^1$ is hydrogen; $R^2$ is selected from hydrogen, methyl, ethyl, fluoro, chloro and methoxy; $R^3$ is hydrogen; and $R^4$ is selected from hydrogen, fluoro and methyl.

1.23 A compound according to Embodiment 1.22A wherein (i) $R^1$ is hydrogen; $R^2$ is selected from methyl, ethyl, fluoro, chloro and methoxy; $R^3$ is hydrogen; and $R^4$ is hydrogen; or (ii) $R^1$ is hydrogen; $R^2$ is hydrogen; $R^3$ is hydrogen; and $R^4$ is methyl; or (iii) $R^1$ is hydrogen; $R^2$ is fluoro; $R^3$ is hydrogen; and $R^4$ is methyl.

1.24 A compound according to Embodiment 1.1 which is selected from compounds Ex. 1 to Ex. 12 in Table 1 below and salts thereof.
TABLE 1
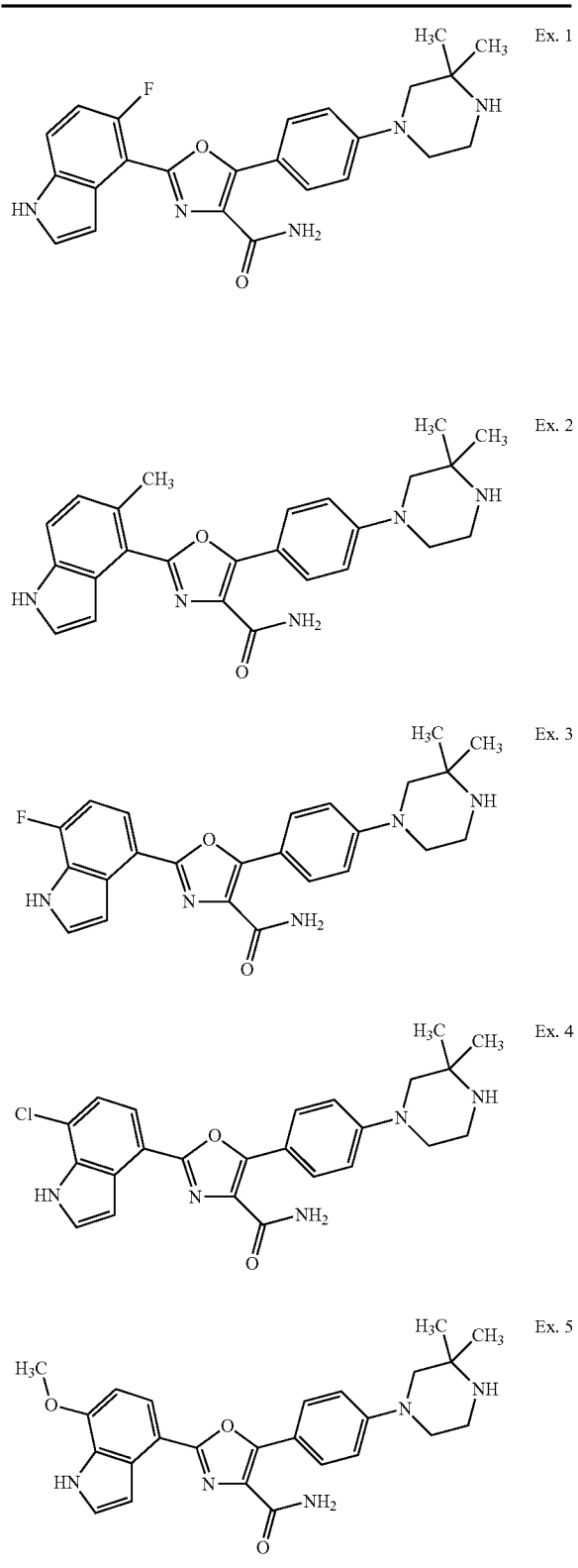
TABLE 1-continued
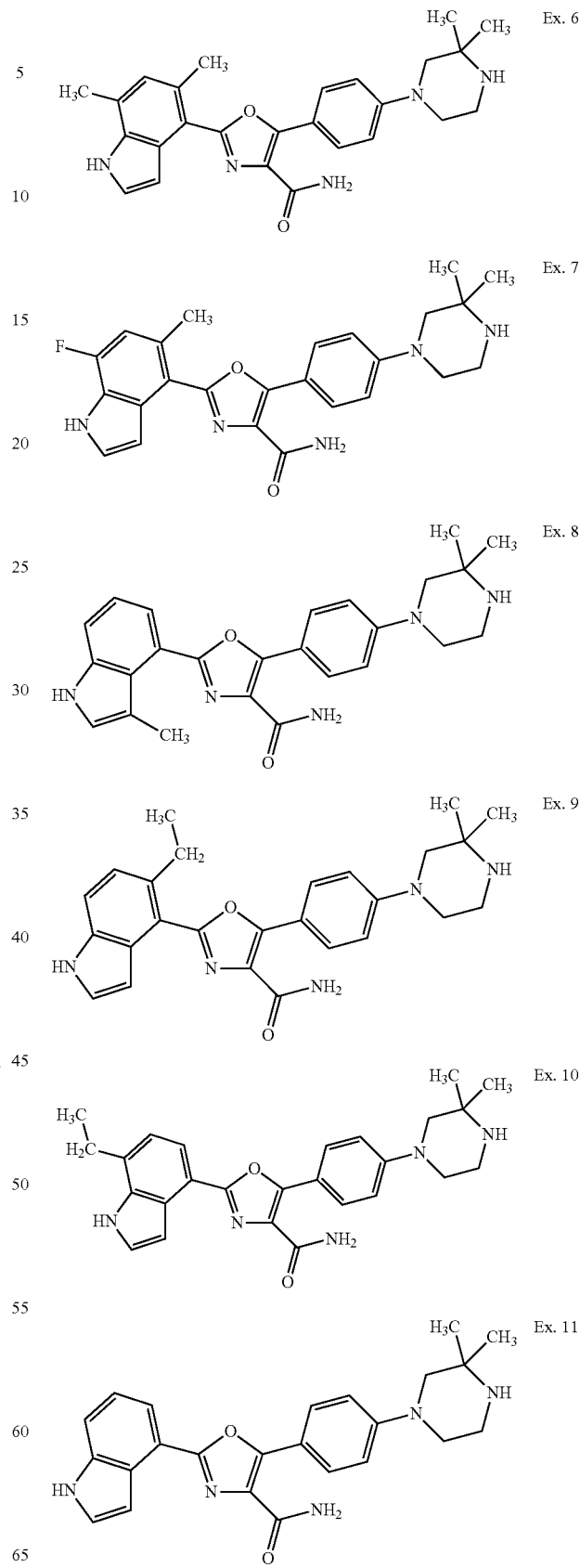

TABLE 1-continued

Ex. 12: [Structure showing F₃C-indole connected to oxazole with phenyl-piperazine (H₃C, CH₃, NH) substituent and C(O)NH₂ group]

1.25 A compound according to Embodiment 1.24 which is selected from compounds Ex. 2, Ex. 3, Ex. 5 and Ex. 7 in Table 1 and salts thereof.
1.26 A compound according to Embodiment 1.25 which is compound Ex. 2 or a salt thereof.
1.27 A compound according to Embodiment 1.25 which is compound Ex. 3 or a salt thereof.
1.28 A compound according to Embodiment 1.25 which is compound Ex. 5 or a salt thereof.
1.29 A compound according to Embodiment 1.25 which is compound Ex. 7 or a salt thereof.
1.30 A compound according to any one of Embodiments 1.1 to 1.29 which is in the form of a free base.
1.31 A compound according to any one of Embodiments 1.1 to 1.29 which is in the form of a salt.
1.32 A compound according to Embodiment 1.31 wherein the salt is an acid addition salt.
1.33 A compound according to Embodiment 1.31 or Embodiment 1.32 wherein the salt is a pharmaceutically acceptable salt.

GENERAL PREFERENCES AND DEFINITIONS

References to kinases herein include not only the normal functioning form of the kinase in question but also mutant forms thereof.

As used herein, the term "modulation", as applied to the activity of a kinase, is intended to define a change in the level of biological activity of the kinase(s). Thus, modulation encompasses physiological changes which effect an increase or decrease in the relevant kinase activity. In the latter case, the modulation may be described as "inhibition".

The term "upregulation" as used herein in relation to a kinase is defined as including elevated expression or overexpression of the kinase, including gene amplification (i.e. multiple gene copies) and increased expression by a transcriptional effect, and hyperactivity and activation of the kinase, including activation by mutations.

References herein to a disease state or condition being "mediated" by a particular kinase are intended to operate limitatively so that the various disease states or conditions to which the term is applied are those in which the kinase (or a mutated form thereof) in question plays a biological role. The biological role played by the kinase may be direct or indirect and may be necessary and/or sufficient for the manifestation of the symptoms of the disease, state or condition (or its aetiology or progression).

Salts

The compounds of the invention may be presented in the form of salts.

The salts (as defined in Embodiments 1.31 to 1.33) are typically acid addition salts.

The salts can be synthesized from the parent compound by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound with the acid in water or in an organic solvent, or in a mixture of the two; generally, nonaqueous media such as ether, ethyl acetate, ethanol, isopropanol, or acetonitrile are used.

Acid addition salts (as defined in Embodiment 1.32) may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, p-toluenesulphonic, undecylenic and valeric acids, as well as acylated amino acids and cation exchange resins.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Isotopes

The compounds of the invention as defined in any one of Embodiments 1.1 to 1.33 may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

In an analogous manner, a reference to a particular functional group also includes within its scope isotopic variations, unless the context indicates otherwise.

For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention (Embodiment 1.34), the compound of any one of Embodiments 1.1 to 1.33 contains no radioactive isotopes. Such compounds are preferred for therapeutic use. In another embodiment (Embodiment 1.35), however, the compound of any one of Embodiments 1.1 to 1.33 may contain one or more radioisotopes. Compounds containing such radioisotopes may be useful in a diagnostic context.

Solvates

Compounds of the formula (1) as defined in any one of Embodiments 1.1 to 1.35 may form solvates.

Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates.

Particularly preferred solvates are hydrates, and examples of hydrates include hemihydrates, monohydrates and dihydrates.

Accordingly, in further embodiments 1.36 and 1.37, the invention provides:

1.36 A compound according to any one of Embodiments 1.1 to 1.35 in the form of a solvate.

1.37 A compound according to Embodiment 1.36 wherein the solvate is a hydrate.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the compound of the invention may be anhydrous. Therefore, in another embodiment (Embodiment 1.38), the invention provides a compound as defined in any one of Embodiments 1.1 to 1.35 in an anhydrous form.

Crystalline and Amorphous Forms

The compounds of any one of Embodiments 1.1 to 1.38 may exist in a crystalline or non-crystalline (e.g. amorphous) state.

Whether or not a compound exists in a crystalline state can readily be determined by standard techniques such as X-ray powder diffraction (XRPD).

Crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD.

Determination of the crystal structure of a compound can be performed by X-ray crystallography which can be carried out according to conventional methods such as those described herein and as described in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal.

In an amorphous solid, the three dimensional structure that normally exists in a crystalline form does not exist and the positions of the molecules relative to one another in the amorphous form are essentially random, see for example Hancock et al. J. Pharm. Sci. (1997), 86, 1).

Accordingly, in further embodiments, the invention provides:

1.39 A compound according to any one of Embodiments 1.1 to 1.38 in a crystalline form.

1.40 A compound according to any one of Embodiments 1.1 to 1.38 which is:

(a) from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

1.41 A compound according to any one of Embodiments 1.1 to 1.38 which is in an amorphous form.

Prodrugs

The compounds of the formula (1) as defined in any one of Embodiments 1.1 to 1.41 may be presented in the form of a pro-drug. By "prodrugs" is meant for example any compound that is converted in vivo into a biologically active compound of the formula (1), as defined in any one of Embodiments 1.1 to 1.41.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Accordingly, in another embodiment (Embodiment 1.42), the invention provides a pro-drug of a compound as defined in any one of Embodiments 1.1 to 1.41 wherein the compound contains a functional group which is convertable under physiological conditions to form a hydroxyl group or amino group.

Complexes and Clathrates

Also encompassed by formula (1) in Embodiments 1.1 to 1.42 are complexes (e.g. inclusion complexes or clathrates with compounds such as cyclodextrins, or complexes with metals) of the compounds of Embodiments 1.1 to 1.42.

Accordingly, in another embodiment (Embodiment 1.43), the invention provides a compound according to any one of Embodiments 1.1 to 1.42 in the form of a complex or clathrate Biological Activity Compounds of the invention have various therapeutic uses.

Accordingly, in another embodiment (Embodiment 2.1), the invention provides a compound of the formula (1) as defined in any one of Embodiments 1.1 to 1.43 for use in medicine.

More particularly, compounds of the invention are inhibitors of kinases, for example FLT3 kinase and Aurora kinases such as Aurora kinase A and Aurora kinase B.

Therefore, in further Embodiments (2.2 to 2.14), the invention provides:

2.2 A compound of the formula (1) or any sub-groups or examples thereof as defined in any one of Embodiments 1.1 to 1.43 for use in the prophylaxis or treatment of a disease state or condition mediated by FLT3 kinase or an Aurora kinase (such as Aurora kinase A or Aurora kinase B).

2.3 A compound of the formula (1) or any sub-groups or examples thereof as defined in any one of Embodiments 1.1 to 1.43 for use in the prophylaxis or treatment of a disease state or condition characterised by abnormal expression (e.g. over-expression) of a FLT3 kinase or an Aurora kinase (such as Aurora kinase A or Aurora kinase B).

2.4 The use of a compound of the formula (1) or any sub-groups or examples thereof as defined in any one of Embodiments 1.1 to 1.43 for the manufacture of a medicament for the prophylaxis or treatment of a disease state or condition mediated by a FLT3 kinase or an Aurora kinase (such as Aurora kinase A or Aurora kinase B).

2.5 The use of a compound of the formula (1) or any sub-groups or examples thereof as defined in any one of Embodiments 1.1 to 1.43 for the manufacture of a medicament for the prophylaxis or treatment of a disease state or condition characterised by abnormal expression (e.g. over-expression) of a FLT3 kinase or an Aurora kinase (such as Aurora kinase A or Aurora kinase B).

2.6 A method for the prophylaxis or treatment of a disease state or condition mediated by a FLT3 kinase or an Aurora kinase (such as Aurora kinase A or Aurora kinase B), which method comprises administering to a subject in need thereof a compound of the formula (1) or any sub-groups or examples thereof as defined in any one of Embodiments 1.1 to 1.43.

2.7 A method for the prophylaxis or treatment of a disease state or condition characterised by abnormal expression (e.g. over-expression) of a FLT3 kinase or an Aurora kinase (such as Aurora kinase A or Aurora kinase B), which method comprises administering to a subject in need thereof a compound of the formula (1) or any sub-groups or examples thereof as defined in any one of Embodiments 1.1 to 1.43.

2.8 A method for alleviating or reducing the incidence of a disease state or condition mediated by a FLT3 kinase or an Aurora kinase (such as Aurora kinase A or Aurora kinase B), which method comprises administering to a subject in need thereof a compound of the formula (1) or any sub-groups or examples thereof as defined in any one of Embodiments 1.1 to 1.43.

2.9 A compound for use, use or method according to any one of Embodiments 2.1 to 2.8 wherein the disease state or condition is one which is mediated by FLT3 kinase or is characterised by abnormal expression (e.g. over-expression) of a FLT3 kinase.

2.10 A compound for use, use or method according to any one of Embodiments 2.1 to 2.8 wherein the disease state or condition is one which is mediated by an Aurora kinase (e.g. Aurora A or Aurora B kinase) or is characterised by abnormal expression (e.g. over-expression) of an Aurora kinase (e.g. Aurora A or Aurora B kinase).

2.11 A method of inhibiting a FLT3 kinase, which method comprises contacting the kinase with a kinase-inhibiting compound of the formula (1) or any sub-groups or examples thereof as defined in any one of Embodiments 1.1 to 1.43.

2.12 A method of inhibiting an Aurora kinase (such as Aurora kinase A or Aurora kinase B), which method comprises contacting the kinase with a kinase-inhibiting compound of the formula (1) or any sub-groups or examples thereof as defined in any one of Embodiments 1.1 to 1.43.

2.13 A method of modulating a cellular process (for example cell division) by inhibiting the activity of a FLT3 kinase using a compound of the formula (1) or any sub-groups or examples thereof as defined in any one of Embodiments 1.1 to 1.43.

2.14 A method of modulating a cellular process (for example cell division) by inhibiting the activity of an Aurora kinase (such as Aurora kinase A or Aurora kinase B) using a compound of the formula (1) or any sub-groups or examples thereof as defined in any one of Embodiments 1.1 to 1.43.

As a consequence of their activity in modulating and in particular inhibiting FLT3 and Aurora kinases, they are expected to be useful in treating or preventing proliferative disorders such as cancers.

Accordingly, in further embodiments (Embodiments 2.15 to 2.28), the invention further provides:

2.15 A compound of the formula (1) or any sub-groups or examples thereof as defined in any one of Embodiments 1.1 to 1.43 for use in the prophylaxis or treatment of a proliferative disease such as a cancer.

2.16 The use of a compound of the formula (1) or any sub-groups or examples thereof as defined in any one of Embodiments 1.1 to 1.43 for the manufacture of a medicament for use in the prophylaxis or treatment of a proliferative disease such as a cancer.

2.17 A method for treating a proliferative disease such as cancer in a subject, which method comprises administering to the subject (e.g. a mammal such as a human) a compound of the formula (1) or any sub-groups or examples thereof as defined in any one of Embodiments 1.1 to 1.43.

2.18 A compound of the formula (1) or any sub-groups or examples thereof as defined in any one of Embodiments 1.1 to 1.43 for use in the prophylaxis or treatment of a disease or condition comprising or arising from abnormal cell growth.

2.19 The use of a compound of the formula (1) or any sub-groups or examples thereof as defined in any one of Embodiments 1.1 to 1.43 for the manufacture of a medicament for use in the prophylaxis or treatment of a disease or condition comprising or arising from abnormal cell growth.

2.20 A method for treating a disease or condition comprising or arising from abnormal cell growth in a mammal, which method comprises administering to the mammal a compound of the formula (1) or any sub-groups or examples thereof as defined in any one of Embodiments 1.1 to 1.43 in an amount effective in inhibiting abnormal cell growth.

2.21 A method for alleviating or reducing the incidence of a disease or condition comprising or arising from abnormal cell growth in a mammal, which method comprises administering to the mammal a compound of the formula (1) or any sub-groups or examples thereof as defined in any one of Embodiments 1.1 to 1.43 in an amount effective in inhibiting abnormal cell growth.

2.22 A compound for use, use or method as defined in any one Embodiments 2.15 to 2.17 wherein the proliferative disease is a cancer selected from a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example acute and chronic myelogenous leukemias, myelodysplastic syndrome, or promyelocytic leukemia; thyroid follicular cancer; a tumour of mesenchymal origin, for example fibrosarcoma or habdomyosarcoma, a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

2.23 A compound for use, use or method as defined in Embodiment 2.22 wherein the cancer is one which is susceptible to inhibition of Aurora A kinase and is selected from breast, bladder, colorectal, pancreatic and ovarian cancers, non-Hodgkin's lymphoma, gliomas, nonendometrioid endometrial carcinomas, Acute Myelogenous Leukemia (AML), Chronic Myelogenous Leukaemia (CML), B-cell lymphoma (Mantle cell), and Acute Lymphoblastic Leukemia (ALL).

2.24 A compound for use, use or method as defined in Embodiment 2.22 wherein the cancer is one which is susceptible to inhibition of Aurora B kinase and is selected from colorectal, lung, Acute Myeloid Leukaemia, Acute Lymphoblastic Leukemia, and Acute Eosinophilic Leukemia.

2.25 A compound for use, use or method as defined in Embodiment 2.22 wherein the cancer is one which is susceptible to inhibition of FLT3 kinase and is Acute Myeloid Leukaemia (AML).

2.26 A compound for use, use or method as defined in Embodiment 2.25 wherein the AML is associated in a patient with a somatic or point mutation of FLT3.

2.27 A compound for use, use or method as defined in Embodiment 2.26 wherein the AML is associated in a patient with a somatic mutation of FLT3 involving internal tandem duplications in a juxtamembrane region of FLT3 receptor.

2.28 A compound for use, use or method as defined in Embodiment 2.26 wherein the AML is associated in a patient with a point mutation of D835 in an activation loop of FLT3.

2.29 A compound for use, use or method as defined in Embodiment 2.22 wherein the proliferative disease is a hematopoietic tumour.

2.30 A compound for use, use or method as defined in Embodiment 2.29 wherein the hematopoietic tumour is selected from acute lymphoblastic leukaemia (ALL), acute myeloid leukaemia (AML), chronic myeloid leukaemia (CML), Hodgkin lymphoma (HL), non Hodgkin Lymphoma (NHL) and multiple myeloma (MM).

Whether or not a particular cancer is one which is sensitive to inhibition by an Aurora kinase or FLT3 kinase may be determined by means of a cell growth assay, for example an assay as described in the example below or by a method as set out in the section headed "Methods of Diagnosis".

The activity of the compounds of the invention as inhibitors of kinases can be measured using the assays set forth in the examples below and the level of activity exhibited by a given compound can be defined in terms of the $IC_{50}$ value. Preferred compounds of the present invention are compounds having an $IC_{50}$ value of less than 0.01 µM, more preferably less than 0.005 µM.

Methods for the Preparation of Compounds of the Invention

In another aspect (Embodiment 3.1), the invention provides a process for the preparation of a compound as defined in any one of Embodiments 1.1 to 1.35, which process comprises:

(i) the reaction of a compound of the formula (10):

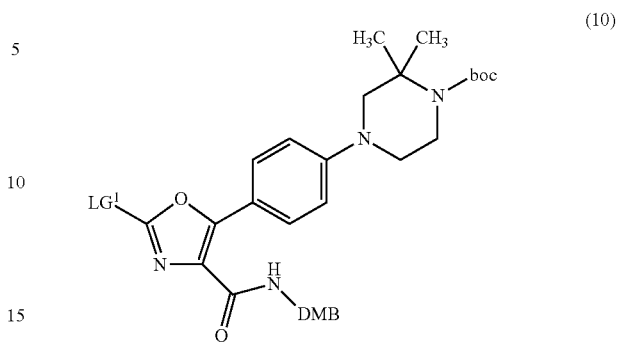

wherein $LG^1$ is iodine or bromine (most typically iodine), DMB is a 2,4-dimethoxybenzyl protecting group and boc is a tert-butyloxycarbonyl protecting group; with a compound of the formula (11A) or (11B) or the corresponding boronate diester:

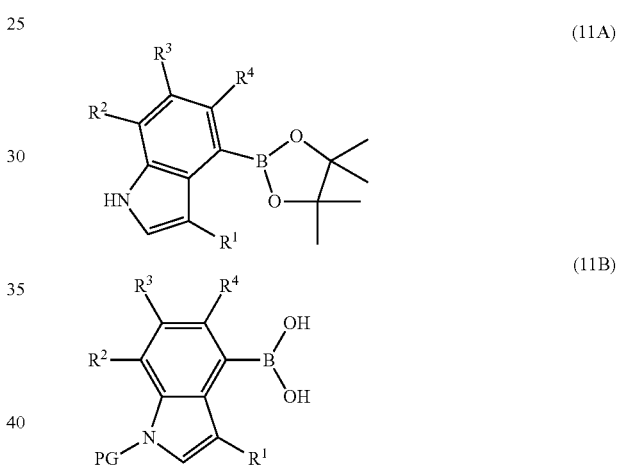

where PG is a protecting group such as a tert-butyldimethylsilyl group under Suzuki coupling reaction conditions, and thereafter removing the protecting groups DMB and boc; or (ii) the reaction of a compound of the formula (18):

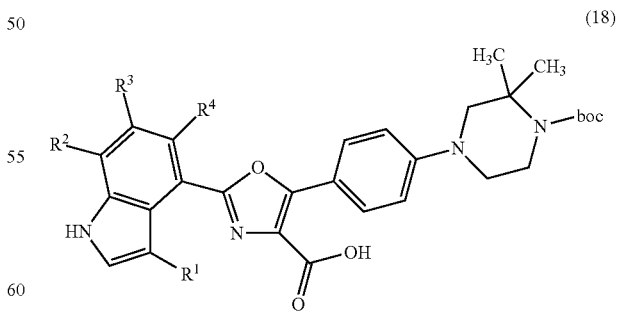

wherein boc is tert-butyloxycarbonyl, with ammonia under amide-forming conditions, and thereafter removing the boc group.

In process variant (i), the Suzuki coupling reaction conditions typically involve the presence of a palladium catalyst such as tetrakis(triphenylphosphine)palladium or bis (1,1'-bis (diphenyl-phosphino)-ferrocene) palladium dichloride (Pd (dppf)$_2$Cl$_2$) and a base (e.g. a carbonate such as potassium carbonate). The reaction may be carried out in a polar solvent, for example acetonitrile or dioxane and mixtures thereof or an aqueous solvent such as aqueous ethanol, or an ether such as dimethoxyethane, and the reaction mixture is typically subjected to heating, for example to a temperature of 80° C. or more, e.g. a temperature in the range 80° C. to 100° C.

After the coupling reaction between compound (10) and either compound (11A) or compound (11B) has taken place, the protecting groups may conveniently be removed using an acid such as trifluoromethanesulphonic acid in a solvent such as dichloromethane, usually at room temperature or thereabouts.

The compound of formula (10) in which LG$^1$ is an iodine atom can be prepared by the series of reactions shown in Scheme 1 below.

In Scheme 1, the iodobenzoyl chloride is reacted with ethyl 2-isocyanoacetate in a polar aprotic solvent such as tetrahydrofuran, for example at room temperature, to give the iodophenyloxazole ester (13). The ester (13) is then reacted with the protected piperazine (14) in the presence of a palladium compound such as palladium acetate and a phosphine ligand such as biphenyl-2-yldicyclohexylphosphine to give the substituted piperazinylphenyl-oxazole ester (15). The reaction is typically carried out in an aprotic solvent such as toluene in the presence of a base such as caesium carbonate, usually with mild heating, for example to a temperature of about 70-90° C.

Scheme 1

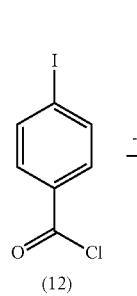

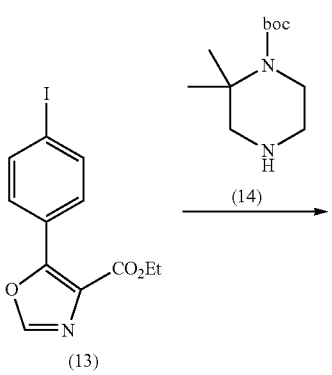

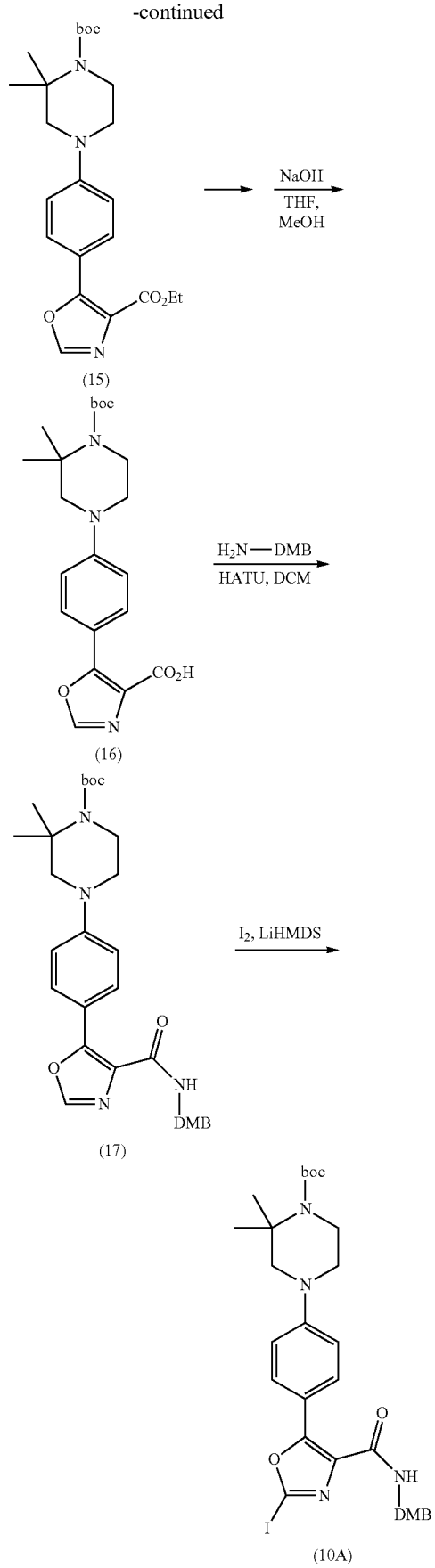

The ester (15) is hydrolysed using an alkali metal hydroxide such as sodium hydroxide in a polar solvent such as a methanol and/or THF to give the carboxylic acid (16) which is then converted to the dimethoxybenzylamide (17) by reaction with dimethoxybenzylamine under amide-forming conditions, for example in the presence of a reagent of the type commonly used in the formation of amide bonds. Examples of such reagents include carbodiimide-based coupling agents such as 1,3-dicyclohexylcarbo-diimide (DCC) (Sheehan et al, *J. Amer. Chem Soc.* 1955, 77, 1067) and 1-ethyl-3-(3'-dimethylaminopropyl)-carbodiimide (referred to herein either as EDC or EDCI) (Sheehan et al, *J. Org. Chem.*, 1961, 26, 2525), which are typically used in combination with 1-hydroxy-7-azabenzotriazole (HOAt) (L. A. Carpino, *J. Amer. Chem. Soc.*, 1993, 115, 4397) or 1-hydroxybenzotriazole (HOBt) (Konig et al, *Chem. Ber.*, 103, 708, 2024-2034). Further examples of such reagents are uronium-based coupling agents such as O-(7-azabenzotriazol-1-yl)-N,N,N,N'-tetramethyluronium hexafluorophosphate (HATU). One preferred amide coupling agent is HATU.

The coupling reaction is typically carried out in a non-aqueous, non-protic solvent such as dimethylformamide at room temperature in the presence of a non-interfering base, for example a tertiary amine such as triethylamine or N,N-diisopropylethylamine.

Lithiation of the dimethoxybenzylamide (17) using lithium hexamethyldisilazide (LiHMDS) in THF at a reduced temperature followed by reaction with iodine gives the 2-iodo-oxazole (10). The compound (10) can then be converted into a compound of the formula (1) by the methods described above.

In process variant (ii), the carboxylic acid of formula (18) is reacted with ammonia (or an amino-group precursor such as dimethoxybenzylamine) under amide-forming conditions of the type described above, for example using EDC in combination with HOBt.

The compound of formula (18) can be prepared by the sequence of reactions shown in Scheme 2 below.

In Scheme 2, the ester (15) (see Scheme 1 above), is iodinated by reaction with lithium hexamethyldisilazide (LiHMDS) in THF at a reduced temperature followed by reaction with iodine to give the iodo compound (19). The iodo compound (19) is then reacted under Suzuki coupling conditions (see above) with a boronate ester compound of the formula (11) to give the intermediate (20) which is hydrolysed using sodium hydroxide to give the carboxylic acid of the formula (18).

Once formed, many compounds of the formula (1) can be converted into other compounds of the formula (1) using standard functional group interconversions.

Examples of functional group interconversions and reagents and conditions for carrying out such conversions can be found in, for example, *Advanced Organic Chemistry*, by Jerry March, 4$^{th}$ edition, 119, Wiley Interscience, New York, *Fiesers' Reagents for Organic Synthesis*, Volumes 1-17, John Wiley, edited by Mary Fieser (ISBN: 0-471-58283-2), and *Organic Syntheses*, Volumes 1-8, John Wiley, edited by Jeremiah P. Freeman (ISBN: 0-471-31192-8).

In many of the reactions described above, it may be necessary to protect one or more groups to prevent a reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

Scheme 2

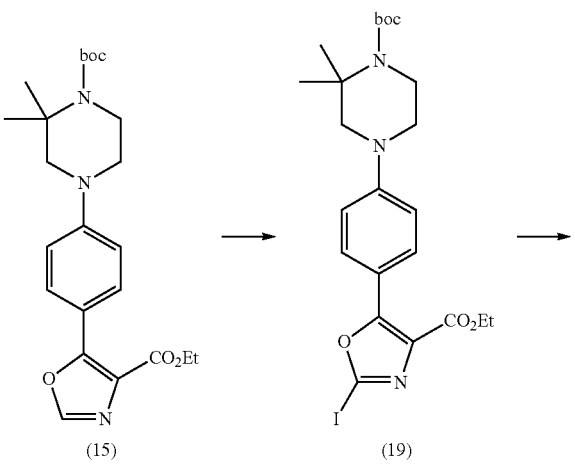

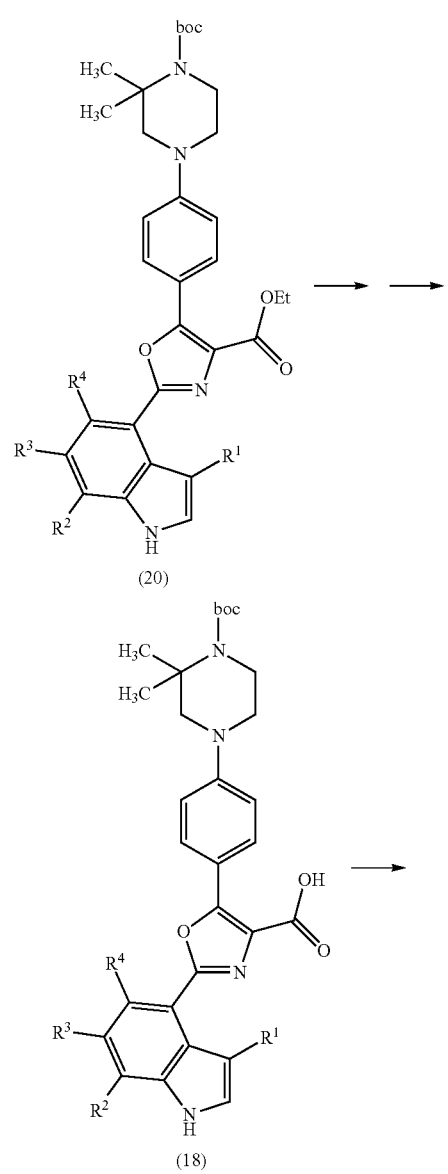

-continued

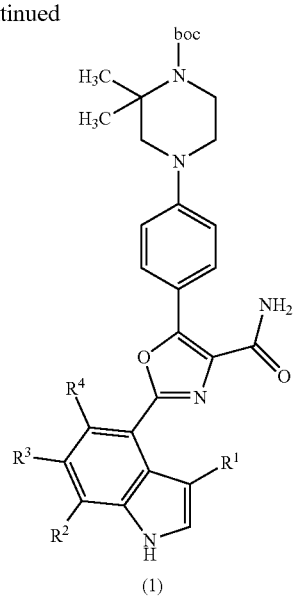

(1)

The compounds of the invention can be isolated and purified according to standard techniques well known to the person skilled in the art. One technique of particular usefulness in purifying the compounds is preparative liquid chromatography using mass spectrometry as a means of detecting the purified compounds emerging from the chromatography column.

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem*.; 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem*.; 2003; 5(3); 322-9.

The intermediate compounds (10), (10A) and (15) to (20) also form part of the present invention. Accordingly, in a further Embodiment (Embodiment 3.2), the invention provides a compound selected from the intermediate compounds of formulae (10), (10A), (15), (16), (17), (18), (19) and (20) as described above.

Pharmaceutical Formulations

While it is possible for the active compound to be administered alone, it is preferable to present it as a pharmaceutical composition (e.g. formulation) comprising at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Accordingly, in another aspect (Embodiment 4.1), the invention provides a pharmaceutical composition comprising a compound as defined in any one of Embodiments 1.1 to 1.43 and a pharmaceutically acceptable carrier.

The term "pharmaceutically acceptable" as used herein refers to compounds, materials, compositions, and/or dosage forms which are, within the scope of sound medical judgment, suitable for use in contact with the tissues of a subject (e.g. human) without excessive toxicity, irritation, allergic response, or other problems or complication, commensurate with a reasonable benefit/risk ratio. Each carrier, excipient, etc. must also be "acceptable" in the sense of being compatible with the other ingredients of the formulation.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery.

In one embodiment (Embodiment 4.2), the pharmaceutical composition is in a form suitable for i.v. administration, for example by injection or infusion.

In another embodiment (Embodiment 4.3), the pharmaceutical composition is in a form suitable for sub-cutaneous (s.c.) administration.

In a further embodiment (Embodiment 4.4), the pharmaceutical composition is in a form suitable for oral administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formula (1) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g. tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastrointestinal tract. Thus, the coating can be selected so as to degrade under certain pH conditions within the gastrointestinal tract, thereby selectively releasing the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Compositions for parenteral administration may be formulated for administration as discrete dosage units or may be formulated for administration by infusion.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the inventions will generally be presented in unit dosage form and, as such, will typically contain sufficient compound to provide a desired level of biological activity. For example, a formulation intended for oral administration may contain from 0.1 milligrams to 2 grams of active ingredient, more usually from 10 milligrams to 1 gram, for example, 50 milligrams to 500 milligrams.

The active compound will be administered to a patient in need thereof (for example a human or animal patient) in an amount sufficient to achieve the desired therapeutic effect.

Methods of Treatment

It is envisaged that the compounds of the formula (1) and sub-groups thereof defined herein will be useful in the prophylaxis or treatment of a range of disease states or conditions mediated by an Aurora kinase (e.g. Aurora a kinase or Aurora B kinase). Examples of such disease states and conditions are set out above.

In particular, it is envisaged that the compounds of formula (1) will be useful in the prophylaxis and treatment of proliferative diseases (such as cancers) and myeloproliferative disorders.

The compounds are generally administered to a subject in need of such administration, for example a human or animal patient, preferably a human.

The compounds will typically be administered in amounts that are therapeutically or prophylactically useful and which generally are non-toxic. However, in certain situations (for example in the case of life threatening diseases), the benefits of administering a compound of the formula (1) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile or continuous manner.

A typical daily dose of the compound can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams) per kilogram of bodyweight although higher or lower doses may be administered where required. Ultimately, the quantity of compound administered and the type of composition used will be commensurate with the nature of the disease or physiological condition being treated and will be at the discretion of the physician.

The compounds of the formula (1) can be administered as the sole therapeutic agent or they can be administered in combination therapy with one of more other compounds for treatment of a particular disease state, for example a neoplastic disease such as a cancer as hereinbefore defined. Examples of other therapeutic agents that may be administered together (whether concurrently or at different time intervals) with the compounds of the formula (1) include but are not limited to topoisomerase inhibitors, alkylating agents, antimetabolites, DNA binders and microtubule inhibitors (tubulin targeting agents), such as cisplatin, cyclophosphamide, doxorubicin, irinotecan, fludarabine, 5FU, taxanes, mitomycin C, or radiotherapy. Alternatively, the compounds of the formula (1) can be administered in a combination therapy with monoclonal antibodies or signal transduction inhibitors.

Where the compound of the formula (1) is administered in combination therapy with one, two, three, four or more other therapeutic agents (preferably one or two, more preferably one), the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

For use in combination therapy with another chemotherapeutic agent, the compound of the formula (1) and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

Methods of Diagnosis

Prior to administration of a compound of the formula (1), a patient may be screened to determine whether a disease or condition from which the patient is or may be suffering is one which would be susceptible to treatment with a compound having activity against a FLT3 kinase or an Aurora kinase (e.g. Aurora a kinase or Aurora B kinase).

Accordingly, in further embodiments (5.1 to 5.6), the invention provides:

5.1: A compound as defined in any one of Embodiments 1.1 to 1.43 herein or any sub-groups or examples thereof as defined herein for use in the treatment or prophylaxis of a disease state or condition in a patient who has been screened and has been determined as suffering from, or being at risk of suffering from, a disease or condition which would be susceptible to treatment with a compound having activity against an Aurora kinase (e.g. Aurora a kinase or Aurora B kinase).

5.2 The use of a compound as defined in any one of Embodiments 1.1 to 1.43 herein or any sub-groups or examples thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against an Aurora kinase (e.g. Aurora a kinase or Aurora B kinase).

5.3 A method for the diagnosis and treatment of a disease state or condition mediated by an Aurora kinase (e.g. Aurora a kinase or Aurora B kinase), which method comprises (i) screening a patient to determine whether a disease or condition from which the patient is or may be suffering is one which would be susceptible to treatment with a compound having activity against the kinase; and (ii) where it is indicated that the disease or condition from which the patient is thus susceptible, thereafter administering to the patient a compound as defined in any one of Embodiments 1.1 to 1.43 herein or any sub-groups or examples thereof as defined herein.

5.4 A compound as defined in any one of Embodiments 1.1 to 1.43 herein or any sub-groups or examples thereof as defined herein for use in the treatment or prophylaxis of a disease state or condition in a patient who has been screened and has been determined as suffering from, or being at risk of suffering from, a disease or condition which would be susceptible to treatment with a compound having activity against FLT3 kinase.

5.5 The use of a compound as defined in any one of Embodiments 1.1 to 1.43 herein or any sub-groups or examples thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against FLT3 kinase.

5.6 A method for the diagnosis and treatment of a disease state or condition mediated by FLT3 kinase, which method comprises (i) screening a patient to determine whether a disease or condition from which the patient is or may be suffering is one which would be susceptible to treatment with a compound having activity against the kinase; and (ii) where it is indicated that the disease or condition from which the patient is thus susceptible, thereafter administering to the patient a compound as defined in any one of Embodiments 1.1 to 1.43 herein or any sub-groups or examples thereof as defined herein.

A biological sample taken from a patient may be subjected to diagnostic tests to determine whether a condition or disease, such as cancer, that the patient is or may be suffering from is one which is characterised by a genetic abnormality (e.g. a mutated kinase) or abnormal protein expression such as over-expression or upregulation of an Aurora kinase or a FLT3 kinase. The patient may be subjected to a diagnostic test to detect a marker characteristic of up-regulation of the Aurora kinase or FLT3 kinase or the presence of a mutated Aurora kinase or FLT3 kinase. Tumours with upregulation of an Aurora kinase or FLT3 kinase may be particularly sensitive to inhibitors of the kinase. Therefore, tumours may preferentially be screened for upregulation of an Aurora kinase or FLT3 kinase. The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, or urine.

Identification of individuals carrying a mutation in an Aurora kinase or FLT3 kinase may mean that the patient would be particularly suitable for treatment with an inhibitor of the kinase. Tumours may preferentially be screened for presence of a variant prior to treatment. The screening process will typically involve direct sequencing, oligonucleotide microarray analysis, or a mutant specific antibody.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel et al., eds. Current Protocols in Molecular Biology (2004) John Wiley & Sons Inc., or Innis, M. A. et al., eds. PCR Protocols: a guide to methods and applications (1990) Academic Press, San Diego. Reactions and manipulations involving nucleic acid techniques are also described in Sambrook et al., $3^{rd}$ Ed, Molecular Cloning: A Laboratory Manual (2001) Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in-situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel et al., eds. Current Protocols in Molecular Biology (2004) John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; (2004) pps. 077-088; Series: Methods in Molecular Medicine.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies.

EXAMPLES

Figure 1:
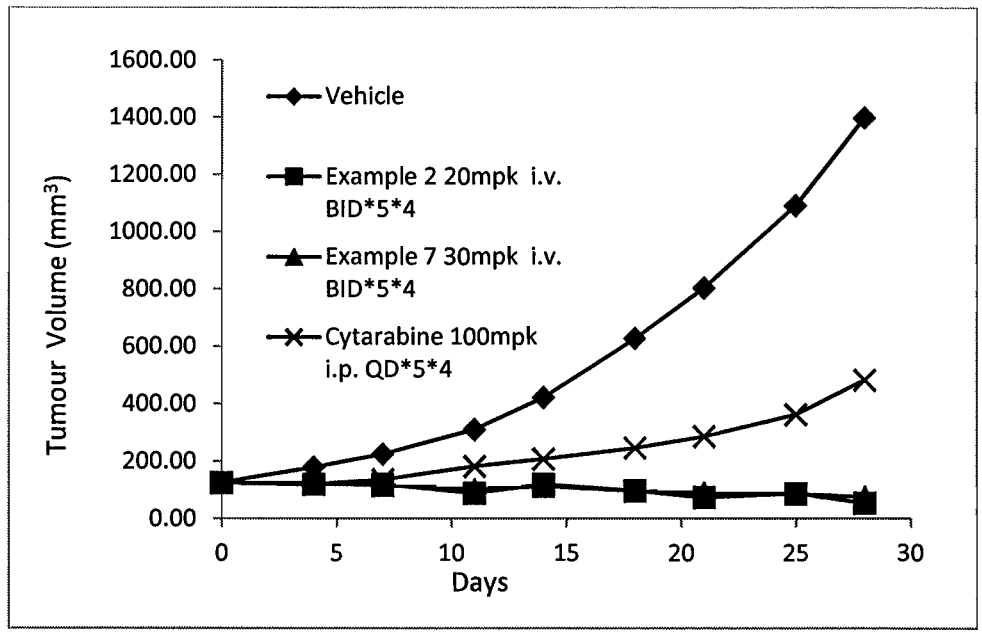
FIG. 1 shows the antitumour effect of the compounds of Examples 2 and 7 compared with cytarabine in the MV4-11 xenograft mouse model described in Example 17.

The invention will now be illustrated, but not limited, by reference to the specific embodiments described in the following examples.

In the examples, the following abbreviations are used.
TEA: Triethylamine
PE: Petroleum ether
EtOAc: Ethyl acetate
STM: Starting material
DMF: N,N-Dimethylformamide
DMSO: Dimethylsulfoxide
DCM: Dichloromethane
LCMS: Liquid chromatography-mass spectrometry
THF: Tetrahydrofuran
prep.HPLC: Preparative HPLC

PREPARATION OF INTERMEDIATES

A. Preparation of Intermediate Compound (10A)

4-{4-[4-(2,4-Dimethoxy-benzylcarbamoyl)-2-iodo-oxazol-5-yl]-phenyl}-2,2-dimethyl-piperazine-1-carboxylic acid tert-butyl ester

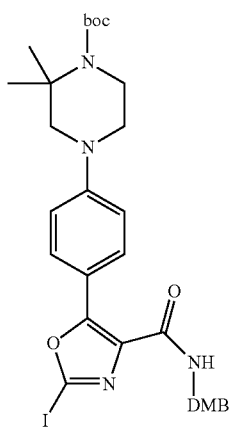

Intermediate compound (10A) can be prepared by the sequence of reactions shown in Scheme 1 above.

Step 1

5-(4-Iodo-phenyl)-oxazole-4-carboxylic acid ethyl ester (Compound (13) in Scheme 1)

To a solution of 4-iodobenzoyl chloride (14.0 g, 0.052 mol) in 100 ml THF was added TEA (15.6 g, 0.156 mol) in a dropwise manner and the mixture was stirred for 10 minutes before slowly adding ethyl 2-isocyanoacetate (6.5 g, 0.058 mol). The reaction mixture was stirred at room temperature for 16 hours, the solvent was removed and the residue was treated with EtOAc and water. The organic layer was separated, dried over $Na_2SO_4$ and the solvent was removed. The crude product was purified by column to give the title compound (11.0 g, 61.7%) as an orange solid.

$^1$H NMR: $CDCl_3$ 400 MHz—δ 7.92 (s, 1H), 7.80~7.90 (m, 4H), 4.43 (q, J=7.2 Hz, 2H), 1.42 (t, J=7.2 Hz, 3H).

Step 2

4-[4-(4-Ethoxycarbonyl-oxazol-5-yl)-phenyl]-2,2-dimethyl-piperazine-1-carboxylic acid tert-butyl ester (Compound (15) in Scheme 1)

To a stirred solution of 5-(4-iodo-phenyl)-oxazole-4-carboxylic acid ethyl ester (11.0 g, 32 mmol) in dry toluene (300 mL) was added 2,2-dimethyl-piperazine-1-carboxylic acid tert-butyl ester (7.53 g, 35.2 mmol), $Pd(AcO)_2$ (580 mg, 2.56 mmol), biphenyl-2-yldicyclohexylphosphine (0.9 g, 2.56 mmol) and $Cs_2CO_3$ (20.7 g, 64 mmol) under a nitrogen atmosphere at room temperature. The mixture was heated to 80° C. and stirred for 24 hrs. The solution was allowed to cool to room temperature and was then partitioned between water and EtOAc. The organic phase was dried over $Na_2SO_4$ and the solvent was removed to give the crude product. It was purified by silica gel column chromatography (PE/EtOAc=40/1~10/1 to recover unreacted starting material; PE/EtOAc=8/1~5/1 to yield the title compound (6.0 g, 43%) as a yellow solid.

$^1$H NMR: DMSO 400 MHz—δ 8.06 (d, J=8.8 Hz, 2H), 7.81 (s, 1H), 6.75 (d, J=9.2 Hz, 2H), 4.42 (q, 2H), 3.86 (m, 2H), 3.50 (m, 2H), 3.46 (s, 2H), 1.56 (s, 9H), 1.43 (s, 6H).

Step 3

4-{4-[4-(2,4-Dimethoxy-benzylcarbamoyl)-oxazol-5-yl]-phenyl}-2,2-dimethyl-piperazine-1-carboxylic acid tert-butyl ester (Compound (17) in Scheme 1)

To a solution of 4-[4-(4-ethoxycarbonyl-oxazol-5-yl)-phenyl]-2,2-dimethyl-piperazine-1-carboxylic acid tert-butyl ester (2.4 g, 5.6 mmol) in 20 mL THF and 20 mL methanol was added 2N aqueous sodium hydroxide solution (11.2 mL, 22.4 mmol). The mixture was stirred at room temperature for 16 hrs and organic solvent was then removed in vacuo. The remaining aqueous mixture was adjusted to pH 4~5 by the addition of 1N aqueous hydrogen chloride. The mixture was freeze-dried to yield 3 g of 4-[4-(4-carboxy-oxazol-5-yl)-phenyl]-2,2-dimethyl-piperazine-1-carboxylic acid tert-butyl ester as an off-yellow powder, which was used in the next step directly.

4-[4-(4-Carboxy-oxazol-5-yl)-phenyl]-2,2-dimethyl-piperazine-1-carboxylic acid tert-butyl ester was dissolved in 30 mL DMF. To the solution was added 2,4-dimethoxybenzylamine (1.26 g, 7.6 mmol), HATU (2.8 g, 7.4 mmol) and TEA (1 g, 10 mmol). The mixture was stirred at room temperature overnight and the solvent was removed in vacuo. The residue was purified by silica gel column chromatography (PE:EtOAc=5:1 to DCM:MeOH=200:1) to afford the title compound (1.6 g, 3 mmol, yield: 54% over two steps).

$^1$HNMR: (400 MHz MeOD) δ 8.10 (d, J=9.2 Hz, 2H), 8.00 (s, 1H), 7.20 (d, J=8.0 Hz, 1H), 6.82 (d, J=9.2 Hz, 2H), 6.48~6.58 (m, 2H), 4.49 (s, 2H), 3.84~3.90 (m, 5H), 3.80 (s, 3H), 3.71 (t, 2H), 3.56 (s, 2H), 1.51 (s, 9H), 1.45 (s, 6H).

Step 4

4-{4-[4-(2,4-Dimethoxy-benzylcarbamoyl)-2-iodo-oxazol-5-yl]-phenyl}-2,2-dimethyl-piperazine-1-carboxylic acid tert-butyl ester (Compound (10A) in Scheme 1))

To a solution of 4-{4-[4-(2,4-dimethoxy-benzylcarbamoyl)-oxazol-5-yl]-phenyl}-2,2-dimethyl-piperazine-1-carboxylic acid tert-butyl ester (2.6 g, 4.7 mmol) in 20 mL THF at −78° C. was added a 1M solution of LiHMDS (44 mL, 44 mmol) in THF. The mixture stirred for 0.5 h, then I$_2$ (9 g, 35 mmol) was added in portions. The mixture was stirred at room temperature for 1 h. The mixture was quenched with 15% aqueous Na$_2$S$_2$O$_3$ and extracted with EtOAc and washed with water. The organic phase was dried over Na$_2$SO$_4$. The solvent was removed in vacuo to give the crude product which was purified by silica gel column chromatography (PE/EtOAc=2/1 to PE/EtOAc/DCM=1/1/2) to afford the title compound (2.4 g, yield: 75%).

$^1$H NMR: CDCl3 400 MHz—δ 8.16 (d, J=9.2 Hz, 2H), 7.22~7.47 (m, 3H), 6.70 (d, J=9.2 Hz, 2H), 6.41~6.46 (m, 3H), 4.52 (d, J=5.6 Hz, 2H), 3.82~3.88 (m, 5H), 3.80 (s, 3H), 3.46 (t, 2H), 3.43 (s, 2H), 1.49 (s, 9H), 1.41 (s, 6H).

B. Preparation of Boronic Acid Intermediates

By following the methods set out below, the following boronic acid/boronate ester intermediates B-1 to B-12 were prepared.

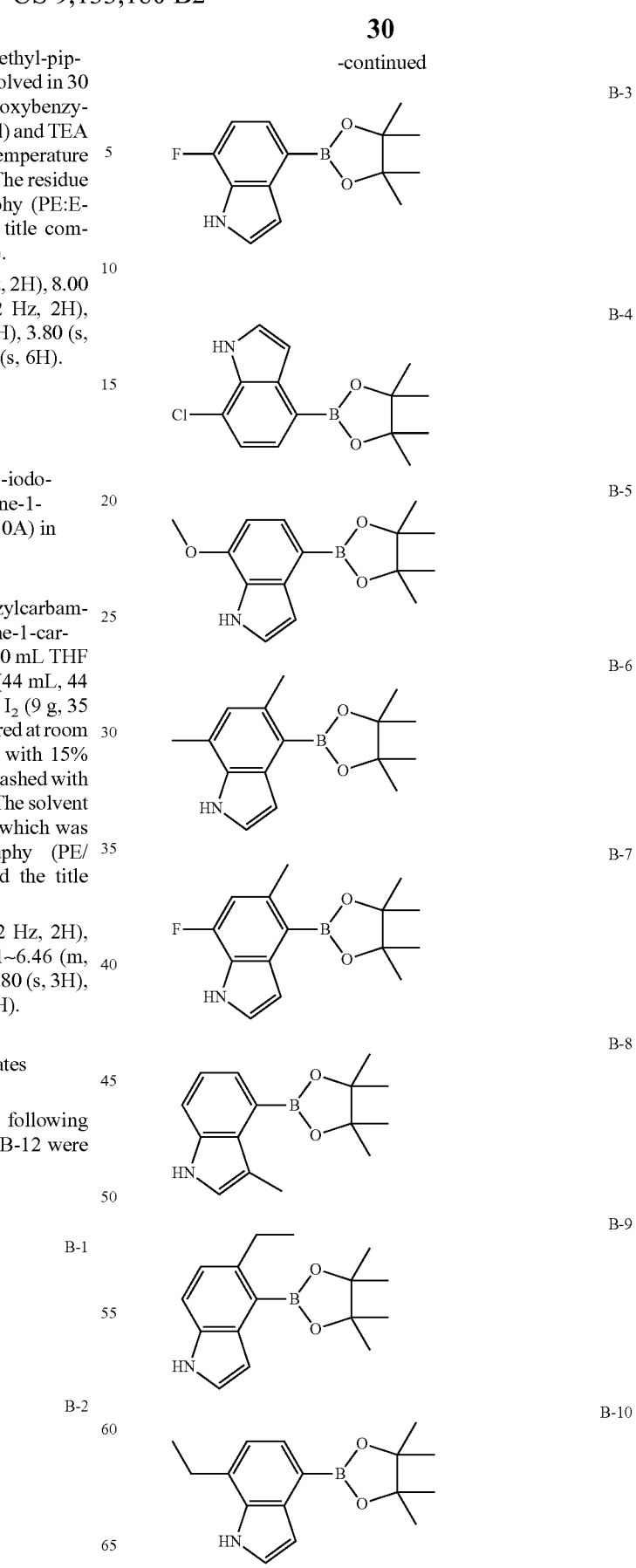

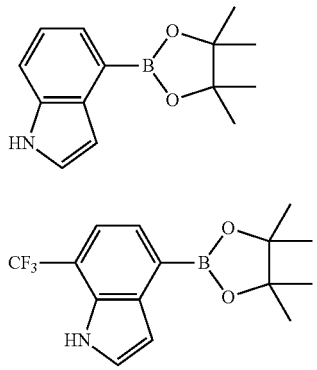

B11

B12

Intermediate B-1

1-(tert-butyldimethylsilyl)-5-fluoro-1H-indol-4-ylboronic acid

Step 1

Preparation of
1-(tert-butyldimethylsilyl)-5-fluoro-1H-indole

At 0° C., NaH (1.88 g, 46.2 mmol) was added to a solution of 5-fluoro-1H-indole (5.2 g, 38.5 mmol) in 40 mL DMF. After 10 min at 0° C. tert-butyldimethylsilyl chloride (6.96 g, 46.2 mmol) was added and the mixture allowed to stir at 0° C. for an additional 1 h. The mixture was warmed to room temperature and stirred overnight, then diluted by the addition of water and extracted with EtOAc. The organic layer was dried over $Na_2SO_4$, concentrated and purified by silica gel column chromatography to give the title compound (6.5 g, 67.7%)

$^1$H NMR $CDCl_3$ 400 MHz δ 7.41 (s, 1H), 7.28-7.25 (dd, 1H, J=2.4 and J=8.8), 7.22 (d, 1H, J=3.2), 6.89 (d, 1H, J=2.8), 6.58-6.57 (dd, 1H, J=0.8 and J=3.2), 0.93 (t, 9H), 0.60 (t, 6H)

Step 2

Preparation of 1-(tert-butyldimethylsilyl)-5-fluoro-1H-indol-4-ylboronic acid

To a mixture of the product of Step 1 (4.98 g, 20 mmol) and TMEDA (2.32 g, 20 mmol) in THF at −78° C. was slowly added a 1.3M solution of s-BuLi (15.4 mL, 20 mmol) in cyclohexane and the mixture was stirred for 2 h at −78° C. Triisopropyl borate (3.76 g, 20 mmol) was added to the mixture at −78° C. and stirred for another 1 h and then warmed to −20° C. Water was added and the mixture was extracted with EtOAc and the organic layer was dried over $Na_2SO_4$ and evaporated. The residue was re-crystallized (EtOAc and n-hexane) to give the title compound (1.2 g, 20.7%).

$^1$H NMR DMSO 400 MHz δ 7.48-7.45 (m, 1H), 7.35 (d, 1H, J=3.2), 6.83 (t, 1H), 6.50 (s, 2H), 6.62 (dd, 1H, J=0.8 and J=3.2), 0.84 (s, 9H), 0.56 (s, 6H).

Intermediate B-2

5-Methyl-4-(4,4,5,5-tetramethyl-[1,3,2]dioxaborolan-2-yl)-1H-indole

Step 1

3-Bromo-2,4-dimethyl-nitrobenzene

Fuming nitric acid (32.5 ml) was slowly added to a solution of 2,6-dimethyl-bromobenzene (10 g, 54 mmol) in AcOH (75 ml) cooled in an ice bath. The resulting mixture was allowed to warm to room temperature, stirred for 1 h, and heated at 80° C. for 2 h. The reaction mixture was cooled to room temperature and poured into ice water with stirring. The resultant precipitate was collected by suction filtration to afford the title compound (10 g) which was used without further purification.

Step 2

[2-(2-Bromo-3-methyl-6-nitro-phenyl)-vinyl]-dimethyl-amine

A mixture of 3-bromo-2,4-dimethyl-nitrobenzene (12 g, 52 mmol) and pyrrolidine (2.12 ml) in DMF/DMA (180 ml) was heated at 120° C. in a sealed tube overnight. The mixture was diluted with water and extracted with EtOAc. The organic layer was dried over $Na_2SO_4$ and concentrated to give the crude title compound (10 g).

Step 3

4-Bromo-5-methylindole

[2-(2-Bromo-3-methyl-6-nitro-phenyl)vinyl]-dimethyl-amine (10 g) was dissolved in $AcOH/H_2O$ (100 mL:25 mL), cooled to 0° C. and treated with Zn (30 g) added slowly in portions. After complete addition, the reaction mixture was heated at 110° C. overnight. The mixture was diluted with water and extracted with EtOAc. The organic layer was dried over $Na_2SO_4$ and concentrated to give the crude product. The crude product was purified by silica gel column chromatography to afford the title compound (1.4 g, 20%)

$^1$H NMR $CDCl_3$ 400 MHz δ 2.47 (m, 3H), 6.50-6.51 (m, 1H), 6.97-6.99 (m, 1H), 7.12-7.18 (m, 2H), 8.12 (s, 1H)

Step 4

Preparation of 5-Methyl-4-(4,4,5,5-tetramethyl-[1,3,2]dioxaborolan-2-yl)-1H-indole 4-Bromo-5-methylindole (0.7 g, 3.35 mmol), bis(pinacolato)diboron (1.7 g, 6.7 mmol), KOAc (1 g, 10 mmol) and $Pd(dppf)Cl_2$ (73 mg, 3 mol %) were suspended in dry DMSO (20 mL) in two 40 mL glass tubes which were tightly sealed with an aluminium/Teflon crimp. The samples were irradiated at 250 W, 180° C. for 40 min in a CEM-Discover monomode microwave reactor. After completion of the reactions, the vessels were cooled down to 60° C., combined and the crude mixture was filtered through a thin plug of celite. The celite plug was washed with EtOAc (50 mL), the organic fractions were combined and the solvent was removed under reduced pressure. The crude product was purified by silica gel column chromatography and then prep-HPLC to give 5 (280 mg, 33%).

¹H NMR CDCl₃ 400 MHz δ 1.41 (s, 12H), 2.63 (s, 3H), 6.96-6.97 (m, 1H), 7.01-7.03 (m, 1H), 7.18-7.20 (m, 1H), 7.32-7.34 (m, 1H), 8.13 (s, 1H)

Intermediate B-3

7-Fluoro-4-(4,4,5,5-tetramethyl-[1,3,2]dioxaborolan-2-yl)-1H-indole

Step 1

Preparation of 4-bromo-7-fluoro-1H-indole

At −40° C., vinylmagnesium bromide (300 mL of 1.0M solution in THF, 300 mmol) was added dropwise to a solution of 3-nitro-4-fluoro-bromobenzene (22 g, 100 mmol) in THF (700 mL). After 1 h at −40° C., the mixture was quenched by aqueous NH₄Cl solution and extracted by EtOAc. The organic layer was dried over Na₂SO₄ and concentrated to give the crude product which was purified by silica gel column chromatography affording 4-bromo-7-fluoro-1H-indole (5 g, 23.3%).

¹H NMR CDCl₃ 400 MHz δ 6.56-6.58 (m, 1H), 6.72-6.79 (m, 1H), 7.06-7.17 (m, 1H), 7.20-7.24 (m, 1H), 8.45 (s, 1H).

Step 2

7-Fluoro-4-(4,4,5,5-tetramethyl-[1,3,2]dioxaborolan-2-yl)-1H-indole

4-Bromo-7-fluoro-1H-indole (5 g, 23.3 mmol), bis(pinacolato)diboron (9.5 g, 37.4 mmol), KOAc (6.85 g, 69.9 mmol) and Pd(dppf)Cl₂ (0.51 g, 3 mol %) were suspended in dry DME (60 mL) in five 40 mL glass tubes which were tightly sealed with an aluminium/Teflon crimp. The samples were irradiated at 250 W, 150° C. for 25 min in a CEM-Discover mono-mode microwave reactor. After completion of the reactions, the vessels were cooled down to 60° C., combined and the crude mixture filtered through a thin layer of celite. The celite was washed with EtOAc (50 mL), the organic fractions were combined and the solvent was removed in vacuo. The crude product was purified by silica gel column chromatography and then prep-HPLC to give the title compound (2 g, 32.9%).

¹H NMR CDCl₃ 400 MHz δ 1.40 (s, 12H), 6.86-6.96 (m, 1H), 7.02-7.14 (m, 1H), 7.20-7.24 (m, 1H), 7.51-7.62 (m, 1H), 8.43 (s, 1H)

Intermediate B-4

7-Chloro-4-(4,4,5,5-tetramethyl-[1,3,2]dioxaborolan-2-yl)-1H-indole

Step 1

Preparation of 4-bromo-1-chloro-2-nitro-benzene

To a solution of 4-chloro-3-nitro-phenylamine (17.2 g, 0.1 mol) in 260 mL HBr (48%) at 0° C. was added dropwise NaNO₂ (13.8 g, 0.2 mol) in water. The reaction mixture was stirred for 1 h at 0° C. then CuBr (24 g, 0.17 mol) was added in portions to the mixture and stirred for an additional 1 h. Water was added, the mixture allowed to warm to room temperature and was then extracted with EtOAc. The crude product was purified by silica gel column chromatography to give the title compound (13 g, 55%).

¹H NMR CDCl₃ 400 MHz δ 8.03-8.02 (m, 1H), 7.66-7.63 (m, 1H), 7.45-7.42 (m, 1H).

Step 2

Preparation of 4-bromo-7-chloroindole

To a solution of 4-bromo-1-chloro-2-nitro-benzene (14 g, 0.059 mol) in 400 mL THF at −40° C. was added dropwise vinylmagnesium bromide (177 mL of 1.0M solution in THF, 0.177 mol). The reaction mixture was stirred for 2 hrs at 40° C. Aqueous NH₄Cl was added and the mixture extracted with ether. The organic phase was dried over Na₂SO₄, concentrated and the residue purified by silica gel column chromatography to give the title compound (6 g, 44%).

¹H NMR CDCl₃ 400 MHz δ 8.5 (s, 1H), 7.31-7.29 (m, 1H), 7.26-7.22 (m, 1H), 7.07-7.05 (m, 1H), 6.65-6.63 (m, 1H).

Step 3

Preparation of 7-chloro-4-(4,4,5,5-tetramethyl-[1,3,2]dioxaborolan-2-yl)-1H-indole 4-Bromo-7-chloroindole (0.6 g, 2.6 mmol), bis(pinacolato)diboron (0.728 g, 2.86 mmol), KOAc (0.76 g, 7.8 mol) and pd(dppf)Cl₂ (57 mg, 3 mol %) were suspended in DME (15 mL) and irradiated at 250 W, 130° C. for 35 min in a CEM-Discover mono-mode microwave reactor. The solid was removed by filtration, water added and the resultant mixture extracted with EtOAc. The organic phase was dried over Na₂SO₄, concentrated and the residue purified by silica gel column chromatography to give the title compound (0.3 g, 39%).

¹H NMR CDCl₃ 400 MHz δ 8.5 (s, 1H), 7.57-7.55 (d, 1H, J=7.6 Hz), 7.3 (s, 1H), 7.21-7.19 (d, 1H, J=7.6 Hz), 7.08-7.07 (m, 1H), 1.396~1.385 (m, 12H).

Intermediate B-5

7-Methoxy-4-(4,4,5,5-tetramethyl-[1,3,2]dioxaborolan-2-yl)-1H-indole

Step 1

Preparation of 4-bromo-3-methyl-2-nitro-phenol

To a solution of 3-methyl-2-nitro-phenol (20 g, 0.13 mol) in CHCl₃ (20 mL) was added a solution of Br₂ (6.4 mL) in HOAc (15 mL) dropwise at 0° C. and the mixture was stirred at 0° C. for 3 h. Ice was added and the mixture was extracted with CHCl₃. After drying over Na₂SO₄, CHCl₃ was removed to give 4-bromo-3-methyl-2-nitro-phenol (30 g) which was used without further purification.

Step 2

Preparation of 1-bromo-4-methoxy-2-methyl-3-nitro-benzene

To a solution of 4-bromo-3-methyl-2-nitro-phenol (30 g, 0.13 mol) in acetone (200 mL) was added K₂CO₃ (39 g, 0.28 mol) and iodomethane (17.6 mL, 0.28 mol). The mixture was stirred for 18 hrs and then it was concentrated, diluted with water and extracted with CH₂Cl₂. The organic phase was dried over Na₂SO₄, filtered and concentrated to give 1-bromo-4-methoxy-2-methyl-3-nitro-benzene (31 g, 96%) which was used without further purification.

Step 3

Preparation of 4-bromo-7-methoxyindole

To a solution of 1-bromo-4-methoxy-2-methyl-3-nitro-benzene (31 g, 0.126 mol) in DMF (150 mL) was added dimethylformamide dimethylacetal (27 mL) and pyrrolidine (10.5 mL, 0.127 mol). The mixture was heated at 90° C. for 18 h and cooled to r.t. The mixture was diluted with water and extracted with $CH_2Cl_2$. The organic phase was dried over $Na_2SO_4$, filtered and concentrated. The residue was dissolved into HOAc (50 mL) and added dropwise to a solution of Fe (20.5 g, 0.37 mol) in boiling HOAc (150 mL). The mixture was refluxed for 1 h and cooled to r.t., water added and the mixture was neutralised with $Na_2CO_3$, and extracted with $CH_2Cl_2$. The organic phase was dried over $Na_2SO_4$, filtered and concentrated. The residue was purified by Prep-TLC (PE/EtOAc=5/1) to give the title compound (13 g, 44%).
$^1$H NMR $CDCl_3$ 400 MHz δ: 8.41 (brs, 1H), 7.18-7.08 (m, 2H), 6.49-6.43 (m, 2H), 3.86 (s, 3H).

Step 4

Preparation of 7-methoxy-4-(4,4,5,5-tetramethyl-[1,3,2]dioxaborolan-2-yl)-1H-indole To a solution of 4-bromo-7-methoxyindole (5 g, 22.2 mmol) in 1,4-dioxane (170 mL) were added bis(pinacolato)diboron (6.2 g, 24.4 mmol), KOAc (6.5 g, 66.3 mmol) and $Pd(dppf)Cl_2$ (1.2 g, 1.7 mmol) and the mixture was heated to reflux for 15 hrs. After cooling the mixture was concentrated and the residue was purified by Preparative TLC (PE/EtOAc=20/1) to give the title compound (2.6 g, 43%).
$^1$H NMR $CDCl_3$ 400 MHz δ: 8.38 (brs, 1H), 7.60 (d, 1H), 7.21 (d, 1H), 7.01 (d, 1H), 6.66 (d, 1H), 3.98 (s, 3H), 1.39 (s, 12H).

Intermediate B-6

5,7-Dimethyl-4-(4,4,5,5-tetramethyl-[1,3,2]dioxaborolan-2-yl)-1H-indole

Step 1

Preparation of 1-bromo-2,4-dimethyl-5-nitro-benzene

1-Bromo-2,4-dimethyl-benzene (9 g, 48.6 mmol) was added to $HNO_3$ (100 mL, 60%) at rt. The mixture was stirred overnight at rt. The mixture was poured into ice-water and extracted with EtOAc. The organic phase was then dried over $Na_2SO_4$ and concentrated to give 1-bromo-2,4-dimethyl-5-nitro-benzene (6.5 g) which was used in the subsequent step without purification.

Preparation of 4-bromo-5,7-dimethylindole

To a solution of 1-bromo-2,4-dimethyl-5-nitro-benzene (7.5 g, 32.6 mmol) in THF (100 mL) at −78° C. was added vinylmagnesium bromide (110 mL of 1.0 M solution in THF, 1.1 mol) dropwise. The reaction was allowed to warm slowly to −40° C. then stirred for 4 h. Water was added, and the reaction mixture allowed to warm slowly to rt and extracted with EtOAc. The organic phase was then dried over $Na_2SO_4$ and concentrated to give 4-bromo-5,7-dimethylindole (2.3 g) which was used in the subsequent step without purification.

Preparation of 5,7-Dimethyl-4-(4,4,5,5-tetramethyl-[1,3,2]dioxaborolan-2-yl)-1H-indole 4-Bromo-5,7-dimethylindole (2.3 g crude, 7 mmol), bis(pinacolato)diboron (2.54 g, 10 mmol), KOAc (2 g, 20 mmol) and $Pd(dppf)Cl_2$ (150 mg, 3 mol %) were suspended in dry DME (30 mL) in five 50 mL glass tubes which were tightly sealed with an aluminium/Teflon crimp. The samples were irradiated at 250 W, 130° C. for 50 min in a microwave reactor. After completion of the reactions, the mixtures were combined, diluted with water and extracted with EtOAc. The organic phase was dried over $Na_2SO_4$ and solvent removed by evaporation. Preparative HPLC afforded the title compound (0.37 g, 15%).
$^1$H NMR: (400 MHz, CDCl3):δ 7.97 (s, 1H), 7.19 (s, 1H), 7.00 (s, 1H), 6.85 (s, 1H), 2.61 (s, 3H), 2.46 (s, 3H), 1.40 (s, 12H)

Intermediate B-7

7-Fluoro-5-methyl-4-(4,4,5,5-tetramethyl-[1,3,2]dioxaborolan-2-yl)-1H-indole

Step 1

Preparation of 1-bromo-4-fluoro-2-methyl-5-nitro-benzene

To a solution of 1-bromo-4-fluoro-2-methyl-benzene (20 g, 0.11 mol) in 160 mL $H_2SO_4$ was added $KNO_3$ (116 g, 0.11 mol) in one portion at 0° C. The mixture was allowed to warm to rt and stirred overnight. The mixture was poured into ice water, extracted with EtOAc, dried over $Na_2SO_4$ and concentrated to give 1-bromo-4-fluoro-2-methyl-5-nitro-benzene (20 g) which was used in the subsequent reaction without purification.

Step 2

Preparation of 4-bromo-7-fluoro-5-methylindole

To a solution of 1-bromo-4-fluoro-2-methyl-5-nitro-benzene (20 g, 0.086 mol) in THF (250 mL) at −78° C. was added vinylmagnesium bromide (300 ml, 0.3 mol) dropwise, then the mixture was stirred at −78° C. for 2 h. Water was added and the reaction allowed to warm slowly to rt. The mixture was extracted with EtOAc, dried over $Na_2SO_4$, and concentrated. The crude product was purified by silica gel column chromatography to afford 4-bromo-7-fluoro-5-methylindole (3.2 g, 16.4%).

Step 3

Preparation of 7-fluoro-5-methyl-4-(4,4,5,5-tetramethyl-[1,3,2]dioxaborolan-2-yl)-1H-indole 4-Bromo-7-fluoro-5-methylindole (3.2 g, 0.014 mol), bis(pinacolato)diboron (5.08 g, 0.02 mol), $Pd(dppf)Cl_2$ (0.1 g) and KOAc (4.1 g, 0.042 mol) were suspended in dry DME (60 mL) in ten 50 mL glass tubes which were tightly sealed with an aluminium/Teflon crimp. The samples were irradiated at 250 W for 2 h at 135° C. in a microwave reactor. The samples were cooled, combined, diluted with water and extracted with EtOAc. The organic phase was dried over $Na_2SO_4$ and solvent removed by evaporation. Preparative HPLC afforded the title compound (0.43 g, 11%).

$^1$H NMR (MDOH 400 MHz)

δ: 7.22-7.21 (d, 1H), 6.87-6.85 (m, 1H), 6.68-6.65 (d, 1H), 2.56 (s, 3H), 1.39 (s, 12H).

Intermediate B-8

3-Methyl-4-(4,4,5,5-tetramethyl-[1,3,2]dioxaborolan-2-yl)-1H-indole

A mixture of 3-methyl-4-bromoindole (0.79 g, 3.8 mmol), bis(pinacolato)diboron (1.1 g, 4.5 mmol), $PdCl_2(dppf)_2$ (83 mg, 0.11 mmol) and KOAc (1.1 g, 11.3 mmol) in DMF (10 mL) was purged under $N_2$ atmosphere for 10 min, followed by heating at 80° C. overnight. The reaction mixture was diluted with water. The aqueous layer was extracted with EtOAc and washed with brine, and dried over anhydrous $Na_2SO_4$. The crude product was purified by silica gel column chromatography to give the title compound (0.7 g, 72%).

$^1$H NMR (400 MHz, $CDCl_3$): δ 7.93 (brs, 1H), 7.57 (d, 1H, J=6.8 Hz), 7.42 (d, 1H, J=8 Hz), 7.17 (t, 1H, J=7.2 Hz), 7.01 (s, 1H), 2.48 (s, 3H), 1.40 (s, 12H).

Intermediate B-9

5-Ethyl-4-(4,4,5,5-tetramethyl-[1,3,2]dioxaborolan-2-yl)-1H-indole

Step 1

Preparation of 6-ethyl-2-methyl-3-nitro-phenylamine

2-Ethyl-6-methyl-phenylamine (21 g, 156 mmol) was dissolved on an ice-bath at 0° C. in 175 mL concentrated $H_2SO_4$. 9 mL (171 mmol, 1.1 eq.) concentrated $HNO_3$ was added and the reaction mixture stirred for 1 h at 0° C. The reaction mixture was poured onto 1 L of ice and the resultant solution extracted 5 times with EtOAc. The combined organic layers were dried over $Na_2SO_4$ and the solvent removed under reduced pressure to yield 19 g (yield 68%) of a mixture of 6-ethyl-2-methyl-3-nitro-phenylamine and by-product 6-methyl-2-ethyl-3-nitro-phenylamine. The mixture was used in the subsequent reaction without further purification.

Step 2

Preparation of 2-bromo-1-ethyl-3-methyl-4-nitro-benzene $NaNO_2$ (7.7 g, 110 mmol) in 15 mL of water was added slowly to a stirred solution of the products of Step 1 (19 g, 106 mmol) in 48% aqueous HBr (35 mL) at 0° C. CuBr (1.4 g, 10 mmol) in 48% aqueous HBr (10 mL) was added dropwise. After stirring for 15 mins, the mixture was heated at 90° C. for 2 hrs. After cooling, the mixture was diluted with water and extracted 5 times with EtOAc. The combined organic phases were concentrated and purified by silica gel column chromatography (PE/EtOAc=50:1) to yield a mixture of 2-bromo-1-ethyl-3-methyl-4-nitro-benzene and 2-bromo-3-ethyl-1-methyl-4-nitro-benzene (23 g, yield 95%).

Step 3

Preparation of 1-[2-(2-bromo-3-ethyl-6-nitro-phenyl)-vinyl]-pyrrolidine

The product of Step 2 (13 g, 53 mmol) and pyrrolidine (2.3 mL) in DMF/DMA (150 ml) were heated at reflux overnight. The mixture was cooled and then concentrated to give the crude title compound, which was used directly in the next step.

Step 4

Preparation of 4-bromo-5-ethyl-1H-indole

A solution of crude 1-[2-(2-bromo-3-ethyl-6-nitro-phenyl)-vinyl]-pyrrolidine from Step 3 in 80 mL of AcOH was added in one portion to a refluxing suspension of iron (13 g) in 50 mL of AcOH. The resultant mixture was refluxed for 2 hrs. After cooling, the mixture was diluted with water and neutralized with $Na_2CO_3$, and extracted 3 times with EtOAc. The combined organic phases were concentrated and purified by silica gel column chromatography and preparative HPLC to yield the title compound (1.5 g, 12% from 6-ethyl-2-methyl-3-nitro-phenylamine).

Step 5

Preparation of 5-ethyl-4-(4,4,5,5-tetramethyl-[1,3,2]dioxaborolan-2-yl)-1H-indole 4-Bromo-5-ethyl-1H-indole (1.0 g, 4.48 mmol), bis(pinacolato)diboron (2.4 g, 9 mmol), KOAc (1.5 g, 15 mmol) and $Pd(dppf)Cl_2$ (210 mg, 6 mol %) were suspended in dry dioxane (50 mL) and heated at 80° C. overnight. The mixture was cooled and filtered and the filtrate was concentrated and purified by preparative HPLC to give the title compound (300 mg, 25%).

$^1$H NMR ($CDCl_3$, 400 MHz): δ 7.90 (brs, 1H), 7.31~7.25 (m, 1H), 7.15~7.08 (m, 1H), 6.98 (d, 1H, J=8.4 Hz), 6.90~9.85 (m, 1H) 2.92 (q, 2H, J=7.6 Hz), 1.34 (s, 12H), 1.16 (t, 3H, J=7.6 Hz).

Intermediate B-10

7-Ethyl-4-(4,4,5,5-tetramethyl-[1,3,2]dioxaborolan-2-yl)-1H-indole

Step 1

Preparation of 4-bromo-1-ethyl-2-nitro-benzene

To a solution of 1-bromo-4-ethylbenzene (7 g, 37.8 mmol) in 9 mL concentrated $H_2SO_4$ at −20° C. was added a mixture of $H_2SO_4$ (3.74 g, 41.9 mmol) and $HNO_3$ (2.64 g, 41.9 mmol). The mixture was stirred at −20° C. for 2 h. Water was added and the mixture was extracted with EtOAc. The organic phase was washed with aqueous $NaHCO_3$ and brine, dried over $Na_2SO_4$ and concentrated. The residue was purified by silica gel column chromatography to give that tile compound (3 g, 34%).

$^1$H NMR (CDCl3 400 MHz)

δ: 8.04-8.035 (d, 1H), 7.68-7.65 (m, 1H), 7.29-7.27 (d, 1H), 2.92-2.87 (m, 2H), 1.31-1.28 (t, 3H).

Step 2

Preparation of 4-bromo-7-ethyl-1H-indole

To a solution of 4-bromo-1-ethyl-2-nitro-benzene (8.7 g, 0.037 mol) in THF at −40° C. was added vinylmagnesium bromide (132 ml, 0.132 mol) dropwise, and the mixture was stirred at −40° C. for a further 2 h. The reaction mixture was diluted with water, extracted with EtOAc, dried over Na$_2$SO$_4$ and concentrated. The crude product was purified by silica gel column chromatography to afford the title compound (1.35 g, 16%).

Step 3

Preparation of 7-Ethyl-4-(4,4,5,5-tetramethyl-[1,3,2]dioxaborolan-2-yl)-1H-indole 4-Bromo-7-ethyl-1H-indole (1.35 g, 6.02 mmol), bis(pinacolato)diboron (3.05 g, 12 mmol), KOAc (1.8 g, 18 mmol) and Pd(dppf)Cl$_2$ (128 mg) were suspended in dry DME (100 mL) and heated at 135° C. overnight. The mixture was cooled and filtered and the filtrate was concentrated and purified by preparative HPLC to give that title compound (300 mg, 25%).

$^1$H NMR (CDCl3 400 MHz)

δ: 8.14 (s, 1H), 7.61-7.60 (d, 1H), 7.28-7.25 (d, 1H), 7.08-7.05 (m, 2H), 2.92-2.86 (m, 2H), 1.38-1.35 (m, 15H).

Intermediate B-11

Commercially Available

Intermediate B-12

7-Trifluoromethyl-4-(4,4,5,5-tetramethyl-[1,3,2]dioxaborolan-2-yl)-1H-indole

Step 1

4-Bromo-7-trifluoromethylindole

To a solution of 4-bromo-2-nitro-1-trifluoromethyl-benzene 11.4 g, 0.04 mol) in 200 mL THF was added vinyl magnesium bromide (160 mL, 0.16 mol) at −78° C. and the mixture was stirred for 1.5 hrs before quenching with a saturated solution of NH$_4$Cl and extracting with EtOAc. The organic phase was dried over Na$_2$SO$_4$ and the solvent removed in vacuo. The crude product was purified by silica gel column chromatography to give the title compound (2 g, 25%). $^1$H NMR (CDCl$_3$ 400 MHz), δ 8.6 (br, 1H), 7.28~7.38 (m, 3H), 6.70 (m, 1H).

Step 2

7-Trifluoromethyl-4-(4,4,5,5-tetramethyl-[1,3,2]dioxaborolan-2-yl)-1H-indole

A mixture of 4-bromo-7-trifluoromethylindole (2 g, 7.6 mmol), bis(pinacolato)diboron (2.5 g, 9 mmol), KOAc (1 g, 0.01 mol) and Pd(dppf)Cl$_2$ (0.2 g) in 30 mL of DMSO was heated at 90° C. under N$_2$ overnight. The residue was partitioned between water and EtOAc. The organic phase was dried over Na$_2$SO$_4$ and the solvent removed in vacuo to give the crude product, which was purified by silica gel column chromatography to give the title compound (1 g, 41%). $^1$H NMR (CDCl$_3$ 400 MHz), δ 8.6 (br, 1H), 7.71 (d, J=7.6 Hz, 1H), 7.47 (d, J=7.6 Hz, 1H), 7.37 (m, 1H), 7.17 (m, 1H), 1.42 (s, 12H)

Preparation of Compounds of the Formula (1)

Example 1

2-(5-Fluoro-1H-Indol-4-yl)-5-[4-(3,3-dimethyl-piperazin-1-yl)-phenyl]-oxazole-4-carboxylic acid amide

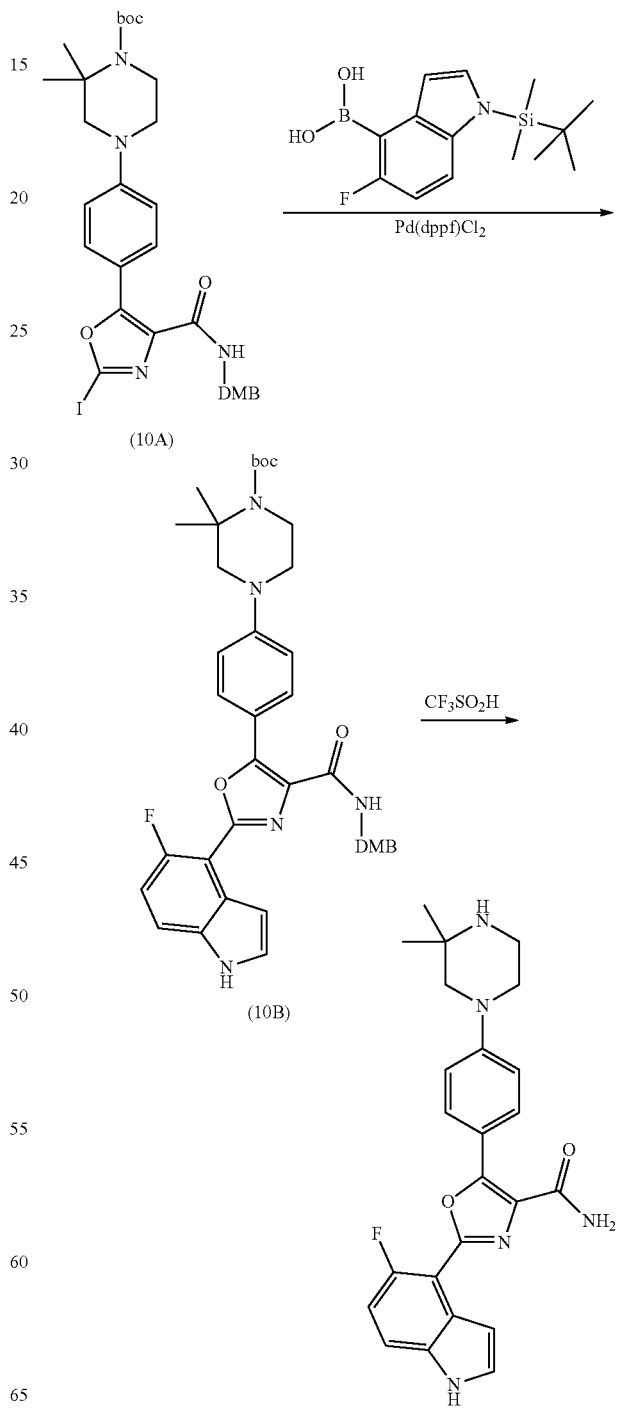

Step 1

To a mixture of Intermediate (10A) (200 mg, 0.3 mmol) in 4 mL dioxane, 1 mL acetonitrile and 1 mL water was added Intermediate B1 (161 mg, 0.55 mmol), K$_2$CO$_3$ (80 mg, 0.6 mmol) and Pd(dppf)Cl$_2$ (36.5 mg, 0.05 mmol). The mixture was heated at 90° C. under N$_2$ for 16 hours. The solvent was removed in vacuo and the residue was purified by preparative TLC (PE:EtOAc=1:1) to afford the desired product 13 (120 mg, 60%).

Step 2

To a solution of 13 (120 mg, 0.18 mmol) in 3 mL CH$_2$Cl$_2$ was added 1 mL triflic acid and the mixture stirred for 4 hours at room temperature. The mixture was then slowly added to saturated aqueous NaHCO$_3$ with stirring, extracted with EtOAc twice. The combined organic phases were concentrated in vacuum. The residue was purified by preparative HPLC to afford the title compound (18 mg, 23%) as an off-white solid.

(18 mg, yield from 10: 14%, M+1: 434)$^1$HNMR (400 MHz DMSO-d6) δ 11.55 (s, 1H), 8.19 (m, 2H), 7.51~7.67 (m, 4H), 7.32 (s, 2H), 7.11 (t, 1H), 6.98 (d, J=8 Hz, 2H), 3.15 (m, 2H), 3.01 (s, 2H), 2.83 (m, 2H), 1.08 (s, 6H).

Example 2

2-(5-Methyl-1H-Indol-4-yl)-5-[4-(3,3-dimethyl-piperazin-1-yl)-phenyl]-oxazole-4-carboxylic acid amide

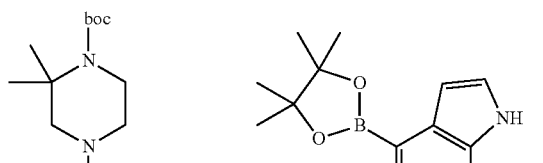

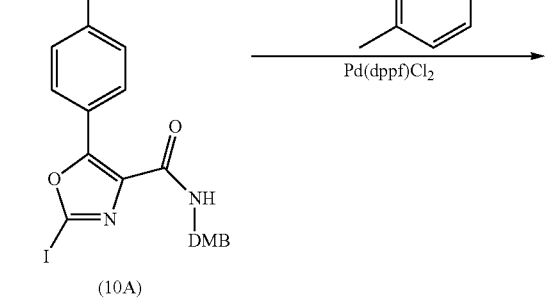

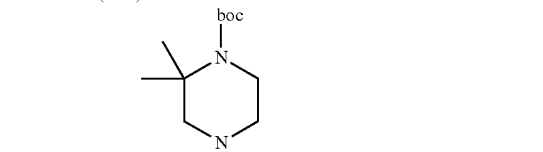

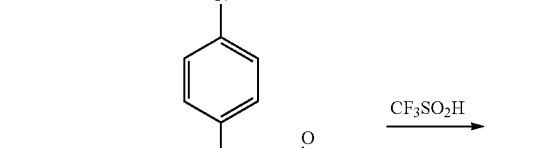

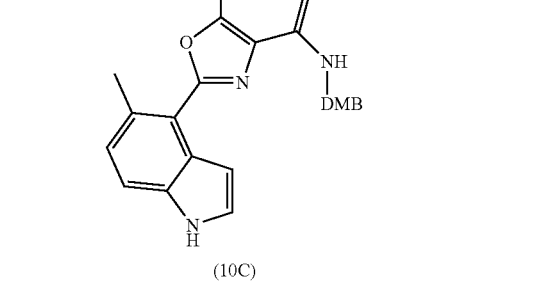

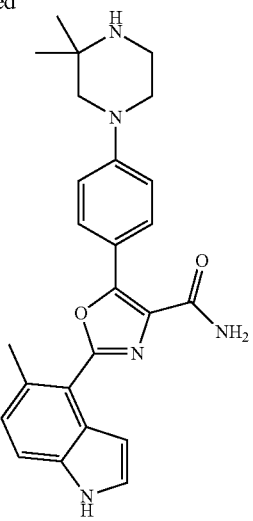

Step 1

To a solution of Intermediate (10A) (1.9 g, 2.8 mmol) in 40 mL dioxane, 10 mL acetonitrile and 10 mL water was added boronic acid ester Intermediate B2 (1 g, 3.9 mmol), K$_2$CO$_3$ (0.7 g, 5.1 mmol) and Pd(dppf)Cl$_2$ (0.5 g, 0.68 mmol). The mixture was heated at 90° C. for 6 hrs under N$_2$. The solvent was removed and the residue was purified by silica gel column chromatography to afford compound 11 (1.32 g, yield: 70%).

Step 2

To a solution of compound 11 (1.32 g, 0.2 mmol) in 20 mL CH$_2$Cl$_2$ was added 5 mL triflic acid. The mixture was stirred at 25° C. for 6 hrs. The mixture was slowly added to aq. NaHCO3 under stirring, and extracted with EtOAc twice. The combined organic phases were concentrated in vacuo. The crude product was purified by preparative HPLC using the system described below to give the title compound (360 mg, 42%) as an off-yellow solid.

(22 mg, yield from 10: 17%, M+1: 430)$^1$HNMR: (400 MHz DMSO-d6) δ 11.3 (s, 1H), 8.22 (d, J=8.8 Hz, 2H), 7.46~7.60 (m, 4H), 7.1 (d, J=8.0 Hz, 1H), 7.00~7.04 (m, 3H), 3.15 (m, 2H), 3.01 (s, 2H), 2.85 (m, 2H), 2.74 (s, 3H), 1.09 (s, 6H).

The prep-HPLC separation method for SRUM-3:
Instrument: Shimadzu LC-8A preparative HPLC
Column: Gemini 250*50 mm i.d. 10 u
Mobile phase: A: H$_2$O (0.04% NH3H2O) B: CH3CN
Gradient: 25%-50% (B phase) in 23 minutes
Flow rate: 80 mL/min
Wavelength: 220 and 254 nm Example 3

2-(7-Fluoro-1H-Indol-4-yl)-5-[4-(3,3-dimethyl-piperazin-1-yl)-phenyl]-oxazole-4-carboxylic acid amide

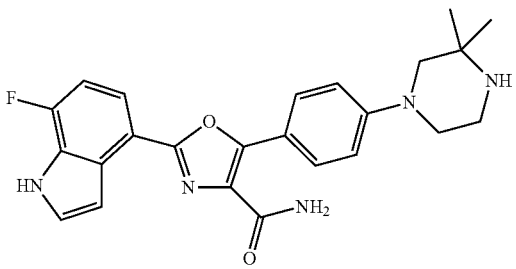 [SMILES: CC1(C)CN(c2ccc(-c3oc(-c4ccc(F)c5[nH]ccc45)nc3C(N)=O)cc2)CCN1]

Prepared by the Method of Example 2 Using Boronic Acid Ester Intermediate B3

(20 mg, yield from 10: 15%, M+1: 434)¹HNMR: (400 MHz DMSO-d6) δ 11.90 (s, 1H), 8.19 (m, 2H), 7.70~7.78 (m, 2H), 7.57 (s, 1H), 7.45 (s, 1H), 7.37 (s, 1H), 7.06 (q, 1H), 6.96 (d, J=8 Hz, 2H), 3.15 (t, 2H), 3.01 (s, 2H), 2.83 (t, 2H), 1.07 (s, 6H).

Example 4

2-(7-Chloro-1H-Indol-4-yl)-5-[4-(3,3-dimethyl-piperazin-1-yl)-phenyl]-oxazole-4-carboxylic acid amide

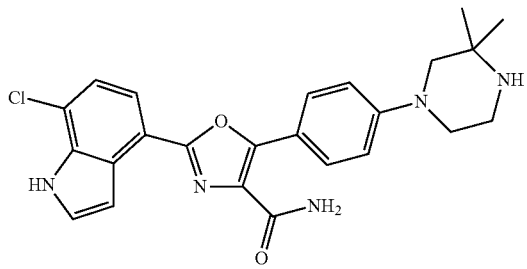 [SMILES: CC1(C)CN(c2ccc(-c3oc(-c4ccc(Cl)c5[nH]ccc45)nc3C(N)=O)cc2)CCN1]

Prepared by the Method of Example 2 Using Boronic Acid Ester Intermediate B4

(24 mg, yield from 10: 18%, M+1: 450)¹HNMR: (400 MHz DMSO-d6) δ 11.85 (s, 1H), 8.24 (d, J=9.2 Hz, 2H), 7.82 (d, J=8.0 Hz, 1H), 7.77 (s, 1H), 7.62 (m, 1H), 7.51 (s, 1H), 7.44 (m, 1H), 7.34 (m, 1H) 7.00 (d, J=9.2 Hz, 2H), 3.16 (t, 2H), 3.01 (s, 2H), 2.85 (t, 2H), 1.08 (s, 6H).

Example 5

2-(7-Methoxy-1H-Indol-4-yl)-5-[4-(3,3-dimethyl-piperazin-1-yl)-phenyl]-oxazole-4-carboxylic acid amide

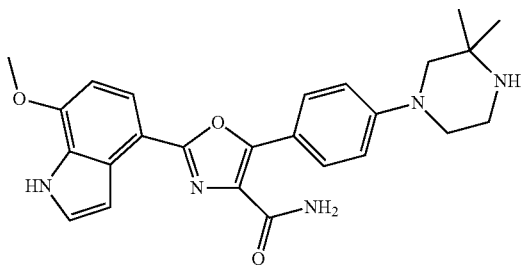

Prepared by the Method of Example 2 Using Boronic Acid Ester Intermediate B5

(19 mg, yield from 10: 14%, M+1: 446)¹HNMR: (400 MHz DMSO-d6) δ 11.58 (s, 1H), 8.23 (d, J=9.2 Hz, 2H), 7.79 (d, J=8.4 Hz, 2H), 7.68 (s, 1H), 7.47 (s, 1H), 7.42 (t, 1H), 7.28 (t, 1H), 7.00 (d, J=9.2 Hz, 2H), 6.84 (d, J=8.0 Hz, 2H), 3.17~3.14 (m, 2H), 3.01 (s, 2H), 2.87 (t, 2H), 2.65 (s, 3H), 1.09 (s, 6H).

Example 6

2-(5,7-Dimethyl-1H-Indol-4-yl)-5-[4-(3,3-dimethyl-piperazin-1-yl)-phenyl]-oxazole-4-carboxylic acid amide

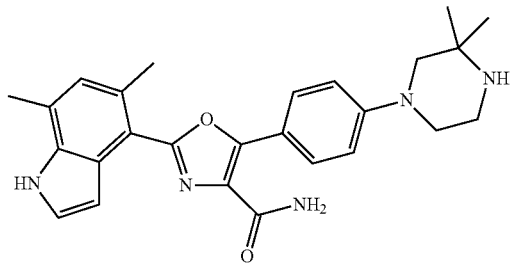

Prepared by the Method of Example 2 Using Boronic Acid Ester Intermediate B6

(33 mg, yield from 10: 25%, M+1: 444)¹HNMR: (400 MHz DMSO-d6) δ 11.3 (s, 1H), 8.21 (d, J=8.8 Hz, 2H), 7.44~7.56 (m, 3H), 6.91~7.05 (m, 4H), 3.15 (m, 2H), 3.01 (s, 2H), 2.85 (m, 2H), 2.70 (s, 3H), 1.08 (s, 6H).

Example 7

2-(5-Methyl-7-Fluoro-1H-Indol-4-yl)-5-[4-(3,3-dimethyl-piperazin-1-yl)-phenyl]-oxazole-4-carboxylic acid amide

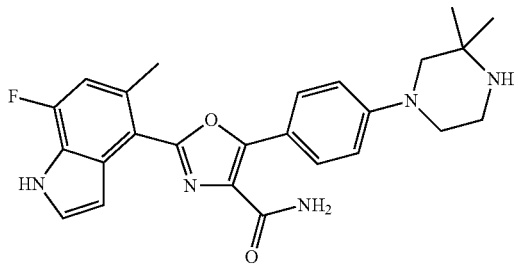

Prepared by the Method of Example 2 Using Boronic Acid Ester Intermediate B7

(16 mg, yield from 10: 12%, M+1: 448)¹HNMR: (400 MHz DMSO-d6) δ 8.21 (d, J=8.8 Hz, 2H), 7.46~7.60 (m, 3H), 6.9~7.1 (m, 3H), 3.15 (m, 2H), 3.01 (s, 2H), 2.85 (m, 2H), 2.72 (s, 3H), 1.09 (s, 6H).

Example 8

2-(3-Methyl-1H-Indol-4-yl)-5-[4-(3,3-dimethyl-piperazin-1-yl)-phenyl]-oxazole-4-carboxylic acid amide

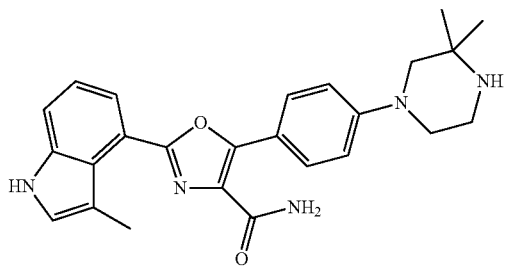 [SMILES: Cc1c[nH]c2cccc(-c3nc(C(N)=O)c(-c4ccc(N5CCNC(C)(C)C5)cc4)o3)c12]

Prepared by the Method of Example 2 Using Boronic Acid Ester Intermediate B8

(9.4 mg, yield from 10: 7%, M+1: 430)$^1$HNMR: (400 MHz DMSO-d6) δ 11.17 (br, 1H), 8.15 (d, J=8.8 Hz, 2H), 7.46~7.60 (m, 4H), 7.29 (s, 1H), 7.16 (t, 1H), 6.97 (d, J=8.8 Hz, 2H), 3.15 (m, 2H), 2.99 (s, 2H), 2.85 (m, 2H), 2.25 (s, 3H), 1.08 (s, 6H).

Example 9

2-(5-Ethyl-1H-Indol-4-yl)-5-[4-(3,3-dimethyl-piperazin-1-yl)-phenyl]-oxazole-4-carboxylic acid amide

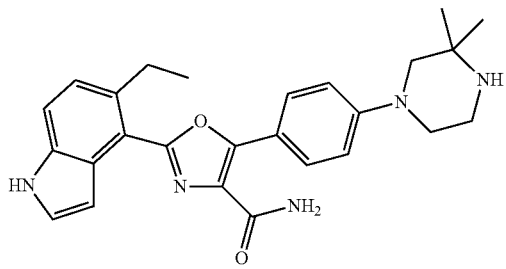 [SMILES: CCc1ccc2[nH]ccc2c1-c1nc(C(N)=O)c(-c2ccc(N3CCNC(C)(C)C3)cc2)o1]

Prepared by the Method of Example 2 Using Boronic Acid Ester Intermediate B9

(28 mg, yield from 10: 21%, M+1: 444)$^1$HNMR: (400 MHz DMSO-d6) δ 11.3 (br, 1H), 8.19 (d, J=8.6 Hz, 2H), 7.46~7.51 (m, 4H), 6.92~7.12 (m, 4H), 3.15 (m, 2H), 3.08 (q, 2H), 3.01 (s, 2H), 2.85 (m, 2H), 1.23 (t, 3H), 1.09 (s, 6H).

Example 10

2-(7-Ethyl-1H-Indol-4-yl)-5-[4-(3,3-dimethyl-piperazin-1-yl)-phenyl]-oxazole-4-carboxylic acid amide

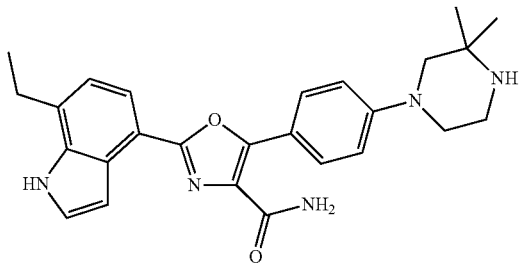 [SMILES: CCc1ccc(-c2nc(C(N)=O)c(-c3ccc(N4CCNC(C)(C)C4)cc3)o2)c2cc[nH]c12]

Prepared by the Method of Example 2 Using Boronic Acid Ester Intermediate B10

(32 mg, yield from 10: 24%, M+1: 443)$^1$HNMR: (400 MHz DMSO-d6) δ 11.4 (br, 1H), 8.23 (d, J=8.6 Hz, 2H), 6.99~7.79 (m, 8H), 3.15 (m, 2H), 3.01 (s, 2H), 2.94 (q, 2H), 2.85 (m, 2H), 1.29 (t, 3H), 1.09 (s, 6H).

Example 11

2-(1H-Indol-4-yl)-5-[4-(3,3-dimethyl-piperazin-1-yl)-phenyl]-oxazole-4-carboxylic acid amide

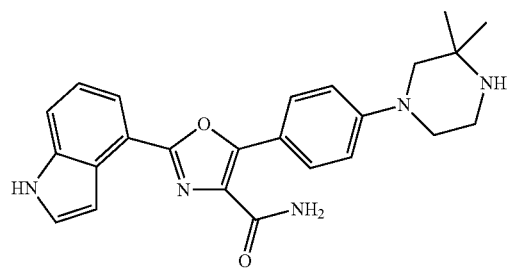 [SMILES: CC1(C)CN(c2ccc(-c3oc(-c4cccc5[nH]ccc45)nc3C(N)=O)cc2)CCN1]

Prepared by the Method of Example 2 Using Boronic Acid Ester Intermediate B11

(466 mg, 38% yield from intermediate 10A, M+1: 416) $^1$HNMR: (400 MHz DMSO-d6) δ 11.48 (s, 1H), 8.27 (d, 2H), 7.85 (d, 1H), 7.74 (s, 1H), 7.61-7.53 (m, 3H), 7.33 (s, 1H), 7.26 (t, 1H), 7.02 (d, 2H), 3.19-3.17 (m, 2H), 3.03 (s, 2H), 2.89-2.86 (m, 2H), 1.11 (s, 6H).

Example 12

2-(7-Trifluoromethyl-1H-Indol-4-yl)-5-[4-(3,3-dimethyl-piperazin-1-yl)-phenyl]-oxazole-4-carboxylic acid amide

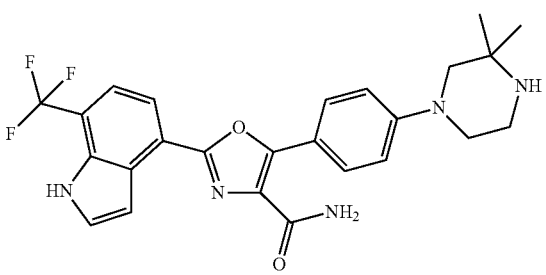 [SMILES: CC1(C)CN(c2ccc(-c3oc(-c4ccc(C(F)(F)F)c5[nH]ccc45)nc3C(N)=O)cc2)CCN1]

The title compound was prepared by the sequence of reactions shown in general Scheme 2 above.

Step 1

Ethyl 5-(4-(4-(tert-butoxycarbonyl)-3,3-dimethylpiperazin-1-yl)phenyl)-2-iodooxazole-4-carboxylate The title compound was prepared from intermediate ethyl ester Compound (15) (see Step 2 in the preparation of Intermediate Compound (10A) above) using the lithiation/iodination method described in Step 4 of the same preparation.

Step 2

4-{4-[4-Ethoxycarbonyl-2-(7-trifluoromethyl-1H-indol-4-yl)-oxazol-5-yl]-phenyl}-2,2-dimethyl-piperazine-1-carboxylic acid tert-butyl ester Ethyl 5-(4-(4-(tert-butoxycarbonyl)-3,3-dimethylpiperazin-1-yl)phenyl)-2-iodooxazole-4-carboxylate was reacted with boronic acid ester intermediate B-12 under Suzuki coupling conditions analogous to those described in Example 2 above to give the title compound.

Step 3

4-{4-[4-Carboxy-2-(7-trifluoromethyl-1H-indol-4-yl)-oxazol-5-yl]-phenyl}-2,2-dimethyl-piperazine-1-carboxylic acid tert-butyl ester 4-{4-[4-Ethoxycarbonyl-2-(7-trifluoromethyl-1H-indol-4-yl)-oxazol-5-yl]-phenyl}-2,2-dimethyl-piperazine-1-carboxylic acid tert-butyl ester (0.2 g, 0.3 mmol) and NaOH (0.024 g, 0.6 mmol) in 5 mL of methanol, water and THF were stirred at 50° C. overnight. The organic solvent was removed in vacuo, the remaining solution adjusted to pH 5, and the resultant title compound was collected as a white solid by filtration, and dried under reduced pressure.

Step 4

4-{4-[4-Carbamoyl-2-(7-trifluoromethyl-1H-indol-4-yl)-oxazol-5-yl]-phenyl}-2,2-dimethyl-piperazine-1-carboxylic acid tert-butyl ester A mixture of 4-{4-[4-carboxy-2-(7-trifluoromethyl-1H-indol-4-yl)-oxazol-5-yl]-phenyl}-2,2-dimethyl-piperazine-1-carboxylic acid tert-butyl ester, EDCI HCl (0.36 g, 0.002 mol) and HOBt (0.3 g, 0.002 mol) in 15 mL of DMF and 15 mL of $NH_3$ in dioxane was stirred for 2 hrs. The solvents were removed in vacuo. The residue was partitioned between water and EtOAc, the organic phase dried over $Na_2SO_4$ and the solvent removed in vacuo to give the crude title compound product (0.18 g crude).

Step 5

2-(7-Trifluoromethyl-1H-Indol-4-yl)-5-[4-(3,3-dimethyl-piperazin-1-yl)-phenyl]-oxazole-4-carboxylic acid amide 4-{4-[4-Carbamoyl-2-(7-trifluoromethyl-1H-indol-4-yl)-oxazol-5-yl]-phenyl}-2,2-dimethyl-piperazine-1-carboxylic acid tert-butyl ester (0.18 g crude) was dissolved in a mixture of DCM and TFA (30 mL 2:1), and the solution was stirred at RT for 2 hrs, when the solvent was removed in vacuo. The residue was partitioned between water and EtOAc. The organic phase was dried over $Na_2SO_4$ and the solvent was removed in vacuo to give the crude product which was purified by prep-HPLC to give the title compound (60 mg, 41% from ethyl 5-(4-(4-(tert-butoxycarbonyl)-3,3-dimethylpiperazin-1-yl)phenyl)-2-iodooxazole-4-carboxylate).

M+1: 484)$^1$HNMR: (400 MHz DMSO-d6) δ 11.85 (s, 1H), 8.27-8.25 (d, 2H, J=8 Hz), 7.97-7.95 (d, 1H, J=8 Hz), 7.85 (s, 1H), 7.66-7.56 (m, 3H), 7.02-7.00 (d, 2H J=0.8 Hz), 3.19-3.17 (m, 2H), 3.04 (s, 2H), 2.87-2.86 (m, 2H), 1.09 (s, 6H).

Biological Activity

Example 13

FLT3 Kinase and Aurora Kinase-Inhibiting Activity

The ability of the compounds of the invention to inhibit FLT3 kinase and Aurora A and Aurora B kinases was determined using the assays described below.

Kinase assays were performed at Reaction Biology Corp., Malvern, Pa., USA, using the following general procedure:
1) Prepare indicated substrate in freshly prepared Base Reaction Buffer (20 mM Hepes pH 7.5, 10 mM $MgCl_2$, 1 mM EGTA, 0.02% Brij35, 0.02 mg/ml BSA, 0.1 mM $Na_3VO_4$, 2 mM DTT, 1% DMSO).
2) Deliver cofactors (1.5 mM $CaCl_2$, 16 ug/mL Calmodulin, 2 mM $MnCl_2$) to the substrate solution above.
3) Deliver indicated kinase into the substrate solution and gently mix
4) Deliver varying concentrations of test compound in DMSO into the kinase reaction mixture.
5) Deliver $^{33}$P-ATP (specific activity 0.01 □Ci/□L final) into the reaction mixture to initiate the reaction.
6) Incubate kinase reaction for 120 min at room temperature.
7) Reactions are spotted onto P81 ion exchange filter paper (Whatman #3698-915)
8) Unbound phosphate is removed by washing filters extensively in 0.75% phosphoric acid.
9) $^{33}$P signal was determined using Typhoon phosphorimagers (GE Healthcare). After subtraction of background derived from control reactions containing inactive enzyme, $IC_{50}$ values were determined using the nonlinear regression function in Prism (Graphpad software).

| Protein Name | HUGO symbol | Substrate | Genbank Accession # | Protein Accession # | Clone | Expression | Tag |
|---|---|---|---|---|---|---|---|
| Aurora A | AURKA | Kemptide | NP_940839 | O14965 | Full-length | Baculovirus in Sf21 insect cells | N-terminal His6 tag |
| Aurora B | AURKB | Kemptide | NP_004208.2 | Q96GD4 | Full-length | Baculovirus in Sf21 insect cells | N-terminal His6 tag |

-continued

| Protein Name | HUGO symbol | Substrate | Genbank Accession # | Protein Accession # | Clone | Expression | Tag |
|---|---|---|---|---|---|---|---|
| FLT3 | FLT3 | Abltide | NP_004110 | P36888 | aa 564-958 | Baculovirus in Sf21 insect cells | C-terminal His6 tag |

Substrates: Kemptide=[H-LRRASLG] Abltide=[EAIYAAP-FAKKK]

The concentrations of test compounds required to inhibit 50% of the enzyme activity ($IC_{50}$) of each of the three kinases are set out in the table below. For comparison purposes, the $IC_{50}$ values for the compound 2-(1H-Indol-4-yl)-5-(4-piperazin-1-yl-phenyl)-oxazole-4-carboxylic acid amide disclosed in Example M-12 of WO2008/139161 are also shown.

| Compound of Example | Aurora A kinase $IC_{50}$ (μM) | Aurora B kinase $IC_{50}$ (μM) | FLT3 kinase $IC_{50}$ (μM) |
|---|---|---|---|
| M-12 | 0.075 | 0.013 | 0.0016 |
| 1 | 0.01462 | 0.02433 | 0.00192 |
| 2 | 0.01357 | 0.0059 | 0.00077 |
| 3 | 0.01936 | 0.00936 | 0.000821 |
| 4 | 0.03404 | 0.01387 | 0.00097 |
| 5 | 0.02053 | 0.00878 | 0.00089 |
| 6 | 0.0884 | 0.01962 | 0.00137 |
| 7 | 0.04254 | 0.00593 | 0.00048 |
| 8 | 0.271 | 0.0142 | 0.00055 |
| 9 | — | — | — |
| 10 | 0.0743 | 0.012 | 0.00067 |
| 11 | 0.04625 | 0.01521 | 0.00154 |
| 12 | 0.016 | 0.014 | 0.0028 |

Example 14

Anti-Proliferative Activity

The anti-proliferative activities of compounds of the invention are determined by measuring the ability of the compounds to inhibit the growth of the colorectal cancer derived cell-line HCT-116. Inhibition of cell growth is measured using the Alamar Blue assay (Nociari et al., *Journal of Immunological Methods* (1998) 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds for a further 96 hours. At the end of the incubation period 10% (v/v) Alamar Blue is added and incubated for a further 6 hours prior to determination of fluorescent product at Excitation 535 nm and Emission 590 nm. All cell lines are obtained from ECACC (European Collection of cell Cultures).

The activities of the compounds of the invention against the human colorectal cancer cell line HCT-116 are shown the in the table below. The column headed HCT-116 96 Hrs refers to the concentration of compound required to reduce the proliferation of HCT-116 cells by 50% following a 96 h period of exposure. The column headed [Polyploidy] refers to the lowest concentration of compound required to produce a distinct polyploid phenotype, believed to be due to Aurora B inhibition.

| Compound of Example | HCT116 96 Hrs $IC_{50}$ (μM) | [Polyploidy] (μM) |
|---|---|---|
| M-12 | 0.68 | 1.0 |
| 1 | 0.24 | 0.3 |
| 2 | 0.074 | 0.03 |
| 3 | 0.12 | 0.1 |
| 4 | 0.26 | 0.3 |
| 5 | 0.087 | 0.1 |
| 6 | 0.16 | 0.1 |
| 7 | 0.12 | 0.1 |
| 8 | — | — |
| 9 | — | — |
| 10 | 0.22 | 0.3 |
| 11 | 0.17 (n = 5) | 0.1 |
| 12 | — | — |

Example 15

Permeability Studies Using Caco-2 Cells

The ability of a compound to be taken up and retained by a cell can be measured by carrying out permeability studies using Caco-2 cells. Although Caco-2 cells are typically used to predict the oral bioavailability of a compound, the measurements obtained are also indicative of the cell penetration ability of a compound.

Compounds of the present invention were therefore tested in a standard Caco-2 assay and the rate of flow of the compounds into and out of the cells was determined. From the results, the efflux ratio was calculated as the ratio of the rate of compound leaving the cell to the rate of compound entering the cell.

The results are set out in the table below. In the table, the column headed "Caco-2 A2B" indicates the rate at which compound flows into the cells and the column Caco-2 B2A indicates the rate at which compound flows out of the cells. The "Efflux Ratio" is the ratio of Caco-2 B2A:Caco-2 A2B.

The results demonstrate that all of the compounds tested have more favourable efflux ratios than the compound of Example M-12 of WO2008/139161. In the case of the compounds of Examples 2 to 11, the efflux ratios are more than five fold better than the efflux ratio of prior art compound M-12.

A comparison of the data for compound M-12 and the compound of Example 11 illustrates that replacing a $CH_2$ group in the piperazine ring with a $C(CH_3)_2$ group dramatically improves the efflux ratio.

| Compound of Example | Caco2 A2B $P_{app}$ (×10$^{-6}$ cms$^{-1}$) | Caco2 B2A $P_{app}$ (×10$^{-6}$ cms$^{-1}$) | Caco2 Efflux ratio |
|---|---|---|---|
| M-12 | 1.13 | 58.3 | 51.7 |
| 1 | 0.707 | 22.8 | 32.2 |
| 2 | 1.98 | 9.91 | 4.99 |
| 3 | 1.17 | 7.76 | 6.62 |
| 4 | 0.64 | 2.76 | 4.32 |
| 5 | 1.36 | 11 | 8.05 |

-continued

| Compound of Example | Caco2 A2B $P_{app}$ (×10⁻⁶ cms⁻¹) | Caco2 B2A $P_{app}$ (×10⁻⁶ cms⁻¹) | Caco2 Efflux ratio |
|---|---|---|---|
| 6 | 0.514 | 2.08 | 4.04 |
| 7 | 0.683 | 2.26 | 3.32 |
| 8 | 2.07 | 9.19 | 4.45 |
| 9 | 0.519 | 3.59 | 6.91 |
| 10 | 0.37 | 2.35 | 6.35 |
| 11 | 2.47 | 12.6 | 5.09 |
| 12 | 0.036 | 1.21 | 33.5 |

Example 16

Activity Against Human Haematological Tumour Cell Lines

The compounds of Examples 2 and 7 were tested against a range of human haematological cell lines using the CellTiter-Blue® assay (#G8081, Promega) according to the manufacturer's instructions. Cells were harvested from exponential phase cultures, counted and plated in 96 well flat-bottom microtiter plates at a cell density of 20,000-90,000 cells/well. After a 24 h recovery period to allow the cells to resume exponential growth, 10 µl of culture medium (four control wells/plate) or of culture medium with test compound were added. The compounds were applied in duplicates at ten concentrations and treatment continued for four days. After treatment of cells, 10 µl/well CellTiter-Blue® reagent was added. Following an incubation period of up to four hours, fluorescence (FU) was measured by using the EnVision Xcite multilabel reader (excitation λ=531 nm, emission λ=615 nm). The compounds were tested in two to four independent experiments for each cell line. The IC$_{50}$ (micromolar) values against each cell line are given in the table below.

| Cell-line | Hematological subtype | Example 2 | Example 7 |
|---|---|---|---|
| CCRF-CEM | ALL | 0.050 | 0.046 |
| CCRF-CEM/VCR | ALL | 0.458 | 0.239 |
| JURKAT | ALL | 0.091 | 0.093 |
| MOLT-4 | ALL | 0.048 | 0.045 |
| HL-60 | AML | 0.064 | 0.052 |
| KG-1 | AML | 0.076 | 0.137 |
| MV4-11 | AML | 0.009 | 0.009 |
| NOMO-1 | AML | 0.095 | 0.061 |
| OCI-AML2 | AML | 0.103 | 0.091 |
| PL-21 | AML | 0.099 | 0.091 |
| EM-2 | CML | 0.604 | 0.493 |
| JURL-MK1 | CML | 0.141 | 0.098 |
| K-562 | CML | 0.326 | 0.219 |
| KCL-22 | CML | 0.417 | 0.366 |
| MEG-01 | CML | 0.633 | 0.468 |
| KM-H2 | HL | 0.189 | 0.137 |
| HUT-78 | NHL | 0.138 | 0.123 |
| RAJI | NHL | 2.852 | 1.801 |
| U-937 | NHL | 0.094 | 0.155 |
| IM-9 | MM | 0.07 | 0.070 |
| L-363 | MM | 0.121 | 0.104 |
| LP-1 | MM | 1.070 | 1.009 |
| NCI-H929 | MM | 0.852 | 1.399 |
| RPMI8226 | MM | 2.136 | 1.299 |

Key
ALL = Acute lymphoblastic leukaemia
AML = Acute myeloid leukaemia
CML = Chronic myeloid leukaemia
HL = Hodgkin lymphoma
NHL = Non Hodgkin Lymphoma
MM = Multiple myeloma

Example 17

Xenograft Studies

The in vivo antitumour activity of compounds of the invention was investigated by examining the effect of the compounds of Examples 2 and 7 on tumour growth in a nude mouse xenograft model of the MV4-11 cancer cell line.
Materials and Methods
2.1. Animals and Reagents
MV4-11 cell line (ATCC, USA); RPMI 1640 medium (Invitrogen, USA); FBS (Invitrogen, Australia); Balb/c nude mouse (Slac Laboratory Animal Co., Ltd., Shanghai, China): female, 18-22 g; HP-6-CD (Sigma, USA).
2.2. Procedure
A total of 52 female nude mice were used. The mice were allowed 3 days of acclimatization period before starting the experiment. Mice were implanted subcutaneously (s.c.) with 200 µl of 1×10⁷ MV4-11 tumour cells in 50% Matrigel in the right flank at the beginning of the study. When tumours reached an average volume of 100-150 mm³, 32 mice out of the 52 were selected based on tumour volume, and randomly assigned to 4 groups prior to dosing. Each treatment group consisted of 8 tumour-bearing animals (n=8/group).
Tumour-bearing mice were treated with the compound of Example 2, the compound of Example 7 or vehicle BID for 5 days on, 2 day off, for 4 cycles. A comparison group of mice were treated with cytarabine once daily for 5 days on, 2 days off, for 4 cycles.
Mice were weighed at each dosing and the tumour sizes recorded twice each week. Mice were observed closely for any overt signs of adverse, treatment-related side effects and these were recorded if and when they were observed.
The tumour size was measured twice weekly in two dimensions using calipers, and the volume was expressed in mm³ using the formula: V=0.5 a×b² where a and b were the long and short diameters of the tumour, respectively.
The test formulations were prepared once weekly by weighing an appropriate amount of test compound into a vial, adding an appropriate volume of 20% HP-β-CD to achieve a final concentration of 2 mg/mL for Example 2 and 3 mg/mL for Example 7 (free base), adjusting the pH to pH 5, vortexing the vial for 5 minutes and then placing the vial in a bath sonicator to ensure that the test formulation was clear.
The experimental design is summarised in the table below.

| | | | Treatment | | | | |
|---|---|---|---|---|---|---|---|
| Test Group | No./sex of Mice | Test Compound | Dose (mg/kg) | Conc. (mg/mL) | Dose Volume (mL/kg) | Vehicle | Route |
| 1 | 10 females | None | n/a | n/a | 10 | 20% HP-β-CD | IV |
| 2 | 10 females | Example 2 | 20 | 2 | 10 | 20% HP-β-CD | IV |

-continued

| Test Group | No./ sex of Mice | Test Compound | Dose (mg/kg) | Conc. (mg/mL) | Dose Volume (mL/kg) | Vehicle | Route |
|---|---|---|---|---|---|---|---|
| 3 | 10 females | Example 7 | 30 | 3 | 10 | 20% HP-β-CD | IV |
| 4 | 10 females | cytarabine | 100 | 10 | 10 | saline | IP |

Test compound storage: Dessicated at 4° C.
Overnight Fast of Animals: No
Comments: N/A
Food returned: ad libitum 2.3. Experimental Endpoint:

Mice were euthanized by $CO_2$ exposure after 4-cycle dose. The tumour volume, weight of dissected tumours, and the mouse body weight were measured and recorded. The tumour inhibitory rate (IR) was calculated by the formula IR=($W_V$−$W_T$)/$W_V$×100%.

The differences in tumour size between the groups were analyzed for significance using the unpaired two-tailed Student's t-test. $P<0.05$ was considered to be statistically significant.

3. Results and Discussion 3.1. Tumour Volumes of MV4-11-Bearing Nude Mice

Figure 2:
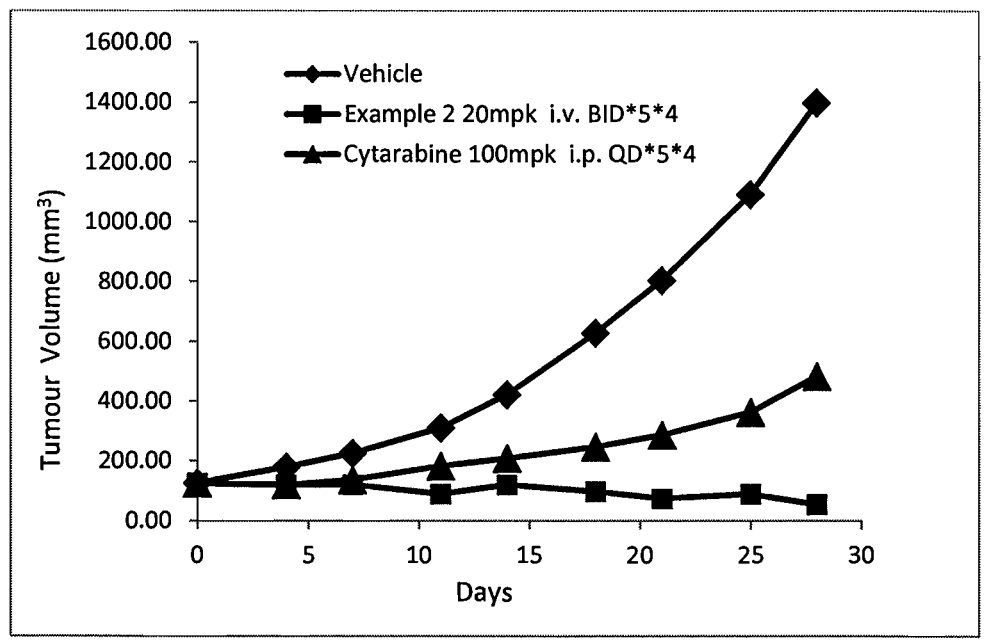
FIG. 2 shows the antitumour effect of the compound of Example 2 compared with cytarabine in the MV4-11 xenograft mouse model.
Figure 3:
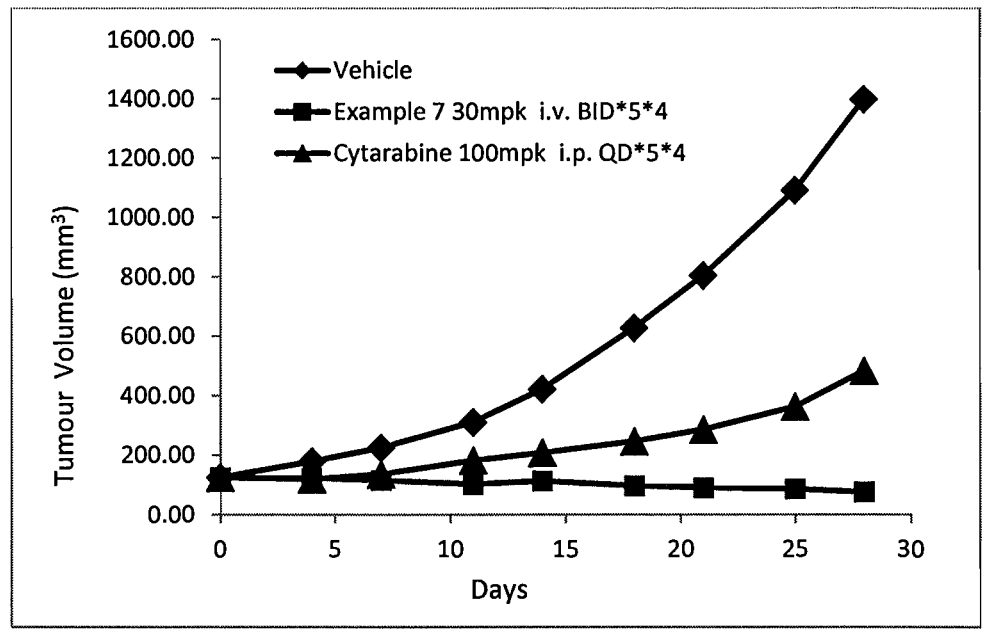
FIG. 3 shows the antitumour effect of the compound of Example 7 compared with cytarabine in the MV4-11 xenograft mouse model.

FIGS. 1 to 3 show the growth inhibition of the compounds of Examples 2 and 7 against MV4-11 xenograft tumors in nude mice. A significant difference in the tumour volume was observed between the tumours on the mice receiving the test compounds and the mice receiving just the vehicle, starting from day 4 (the first measurement) after the first administration of the compounds and persisting till the end. A significant difference in tumour volume was also observed between the tumors on the mice receiving the test compounds (Examples 2 and 7) and the cytarabine treatment group, starting from day 11 after the first administration, and persisting thereafter. FIG. 1 also shows that both Example 2 and Example 7 completely inhibited the tumor growth, while cytarabine slowed down but did not completely block the tumour growth.

3.2. Tumour Weights of MV4-11-Bearing Nude Mice

Figure 4:
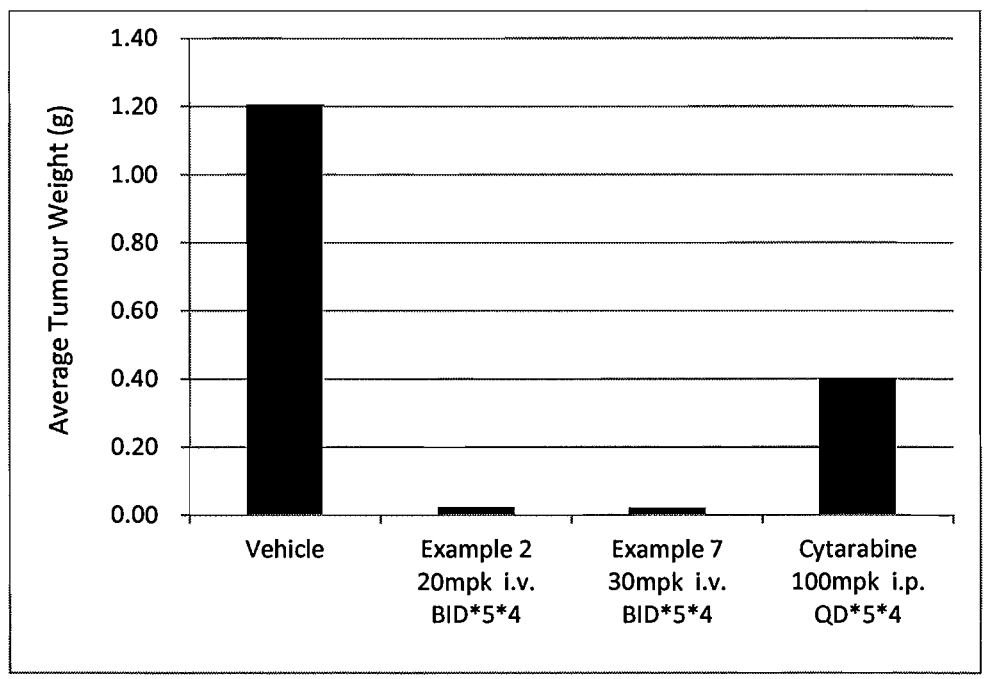
FIG. 4 shows the tumour weights of MV4-11 xenograft-bearing nude mice on day 29 (end point) after the administration of vehicle, the compounds of Examples 2 and 7 and cytarabine.

The tumour inhibition effect of the compounds of Examples 2 and 7 against MV4-11 xenograft tumour growth was further confirmed by the significant difference in tumour weights between the treatment and vehicle groups (FIG. 4) taken at the end point by sacrificing tumour-bearing nude mice.

3.3. Body Weight Change (%) of MV4-11-Bearing Nude Mice

Figure 5:
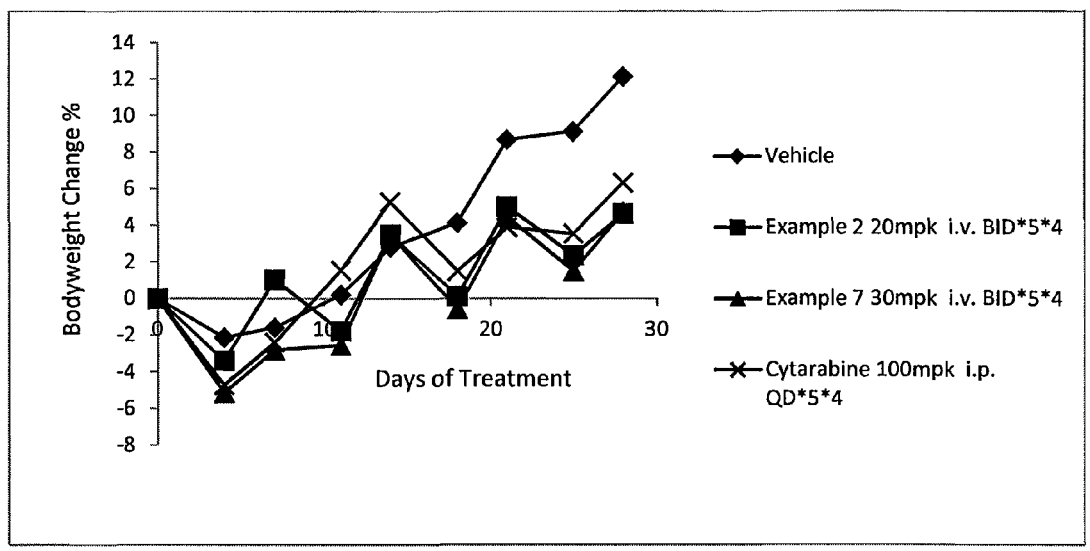
FIG. 5 shows the body weight changes of MV4-11 xenograph-bearing nude mice during the whole study period of the study described in Example 17 after administration of vehicle, the compounds of Examples 2 and 7 and cytarabine.

FIG. 5 shows the body weight change (%) during the whole study period. All treated mice lost around 5% of their body weights during the first few days and then recovered, indicating that the test compounds were well tolerated at current dosages and dosing routes in nude mice.

3.4. The Tumour Inhibitory Rate (IR) Calculation

Compound of Example 2-20 mg/kg group: IR=98.13%
Compound of Example 7-30 mg/kg group: IR=98.24%
Cytarabine—100 mg/kg group: IR=66.72%

4. Conclusions

The effects of the compounds of Example 2 and Example 7 on tumour growth in nude mouse xenograft models from the MV4-11 cancer cell line were investigated in this study. The body weights of MV4-11-bearing nude mice were monitored as an index to reflect in vivo toxicity. The differences in tumour volumes between the test compound (Examples 2 and 7) treatment groups and the vehicle control group as well as the cytarabine comparison group were significant. In this study, both Example 2 and Example 7 inhibited tumour growth completely, while Cytarabine just slowed down but did not completely block the tumour growth. The significant differences in tumour weights between the treatment and vehicle groups further confirmed the antitumour effect. The IR values for the Example 2 group, the Example 7 group and the cytarabine group were 98.13%, 98.24%, and 66.72%, respectively.

The body weight fluctuation profiles revealed that mice receiving test compounds lost body weight during the first few days but then their weights recovered thereafter, thereby indicating that the test compounds were well tolerated at current dosages and dosing routes in nude mice. In conclusion, both the compound of Example 2 at a dose of 20 mg/kg and the compound of Example 7 at a dose of 30 mg/kg, IV, BID were effective inhibitors of MV4-11 xenograft tumor growth without any obvious toxicity.

Pharmaceutical Formulations

Example 18

(i) Tablet Formulation

A tablet composition containing a compound of the formula (1) is prepared by mixing 50 mg of the compound with 197 mg of lactose (BP) as diluent, and 3 mg magnesium stearate as a lubricant and compressing to form a tablet in a known manner.

(ii) Capsule Formulation

A capsule formulation is prepared by mixing 100 mg of a compound of the formula (1) with 100 mg lactose and filling the resulting mixture into standard opaque hard gelatin capsules.

(iii) injectable Formulation I

A parenteral composition for administration by injection can be prepared by dissolving a compound of the formula (1) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (1) (e.g. in salt form) (2 mg/mL) and mannitol (50 mg/mL), sterile filtering the solution and filling into sealable 1 mL vials or ampoules.

(iv) Subcutaneous Infection Formulation

A composition for sub-cutaneous administration is prepared by mixing a compound of the formula (1) with pharmaceutical grade corn oil to give a concentration of 5 mg/mL. The composition is sterilised and filled into a suitable container.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A compound having the formula (1):

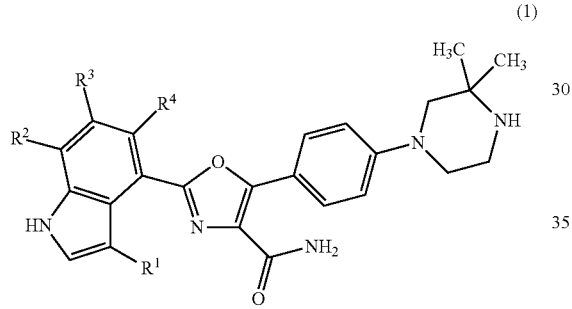

and salts thereof; wherein:

$R^1$ is hydrogen or $C_{1-2}$ alkyl; and $R^2$, $R^3$ and $R^4$ are the same or different and each is selected from the group consisting of hydrogen, $C_{1-2}$ alkyl, fluorine, chlorine, $C_{1-2}$ alkoxy and trifluoromethyl, provided that no more than two of $R^2$, $R^3$ and $R^4$ are other than hydrogen.

2. A compound according to claim 1 wherein $R^1$ is selected from hydrogen and methyl.

3. A compound according to claim 1 wherein $R^2$ is selected from hydrogen, fluorine, chlorine, methyl, ethyl and methoxy.

4. A compound according to claim 1 wherein $R^3$ is hydrogen.

5. A compound according to claim 1 wherein $R^4$ is selected from hydrogen, fluorine, methyl and ethyl.

6. A compound according to claim 1 wherein (i) $R^1$ is hydrogen; $R^2$ is selected from methyl, ethyl, fluoro, chloro and methoxy; $R^3$ is hydrogen; and $R^4$ is hydrogen; or (ii) $R^1$ is hydrogen; $R^2$ is hydrogen; $R^3$ is hydrogen; and $R^4$ is methyl; or (iii) $R^1$ is hydrogen; $R^2$ is fluoro; $R^3$ is hydrogen; and $R^4$ is methyl.

7. A compound according to claim 1 which is selected from compounds Ex. 1 to Ex. 12 in the table below and salts thereof:

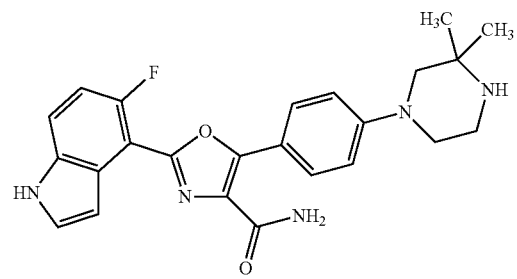

Ex. 1

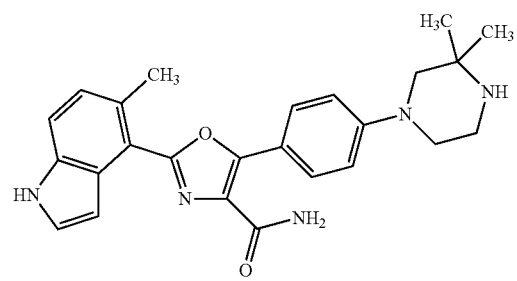

Ex. 2

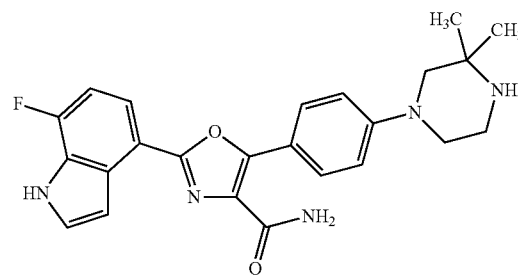

Ex. 3

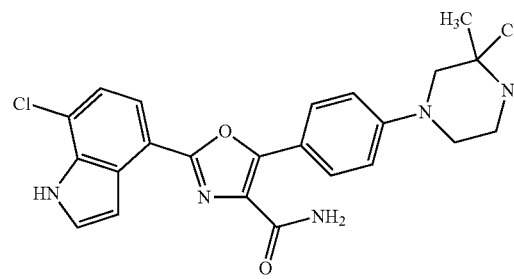

Ex. 4

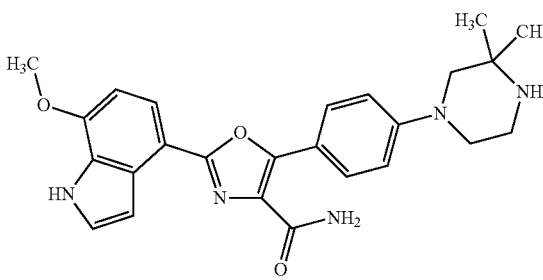

Ex. 5

Ex. 6
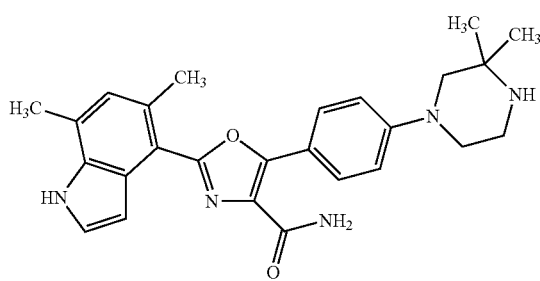

Ex. 7
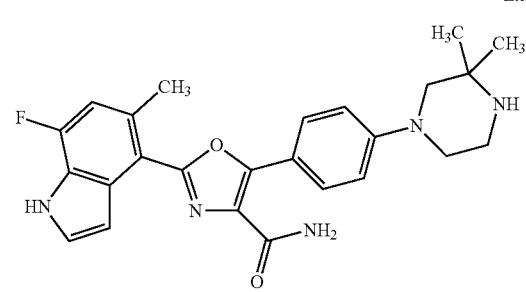

Ex. 8
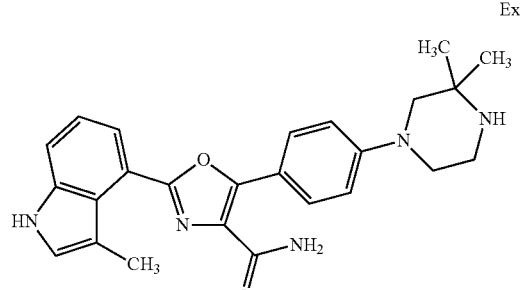

Ex. 9
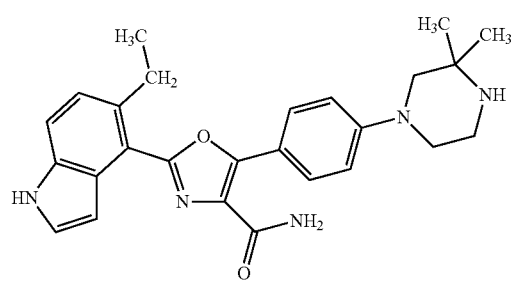

Ex. 10
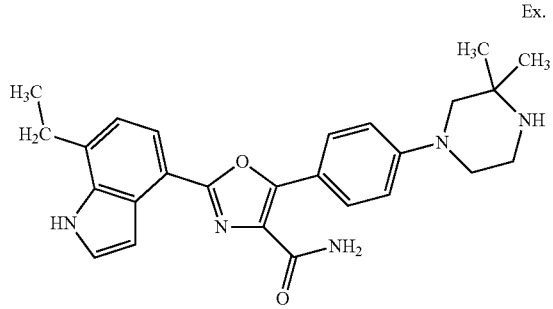

Ex. 11
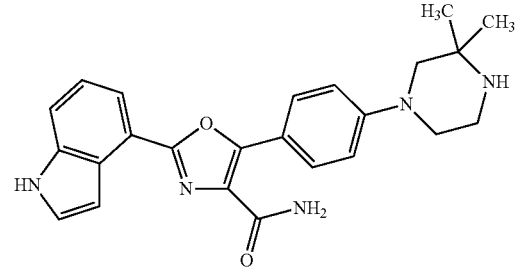

Ex. 12
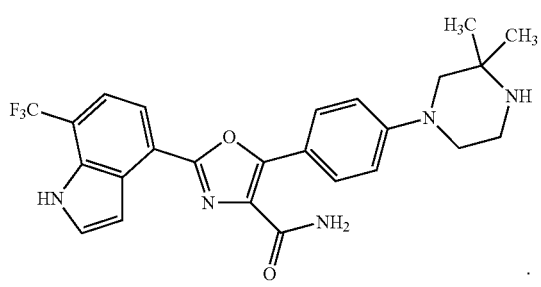

8. A compound according to claim 7 which is selected from Ex. 2, Ex. 3, Ex. 5 and Ex. 7.

9. A pharmaceutical composition comprising a compound as defined in claim 1 and a pharmaceutically acceptable excipient.

10. A compound according to claim 1 wherein $R^1$ is hydrogen, $R^2$ is selected from hydrogen and fluorine; $R^3$ is hydrogen and $R^4$ is methyl.

11. A compound according to claim 10 wherein $R^2$ is hydrogen.

12. A compound according to claim 10 wherein $R^2$ is fluorine.

13. A method for treating a proliferative disease selected from the group consisting of acute lymphoblastic leukemia, acute myeloid leukaemia, chronic myeloid leukaemia, Hodgkin lymphoma, non Hodgkin lymphoma and multiple myeloma, in a subject in need thereof, which method comprises administering to the subject an effective amount of compound having the formula (1):

(1)

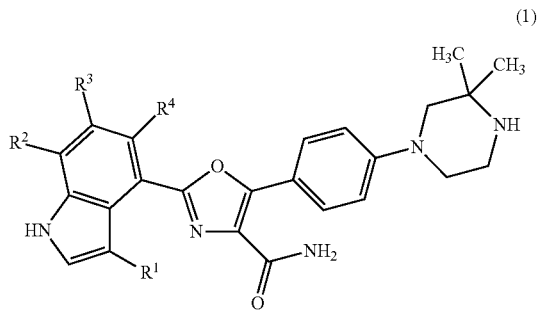

or a salt thereof; wherein:
$R^1$ is hydrogen or $C_{1-2}$ alkyl; and
$R^2$, $R^3$ and $R^4$ are the same or different and each is selected from hydrogen, $C_{1-2}$ alkyl, fluorine, chlorine, $C_{1-2}$ alkoxy and trifluoromethyl, provided that no more than two of $R^2$, $R^3$ and $R^4$ are other than hydrogen.

14. A method of inhibiting a FLT3 kinase or an Aurora kinase, which method comprises contacting the kinase with a kinase-inhibiting compound as defined in claim 1.

15. A combination of a compound as defined in claim 1 and another anti-cancer agent.

* * * * *